(12) United States Patent
Kobayashi et al.

(10) Patent No.: US 6,458,548 B2
(45) Date of Patent: Oct. 1, 2002

(54) CONTAINERS AND KITS FOR THE DETERMINATION OF CELL FUNCTIONS, AND METHOD FOR THE DETERMINATION THEREOF

(75) Inventors: Koji Kobayashi; Yuji Setoguchi; Kiyoshi Kuriyama, all of Osaka (JP)

(73) Assignee: Sekisui Kagaku Kogyo Kabushiki Kaisha, Osaka (JP)

( * ) Notice: Subject to any disclaimer, the term of this patent is extended or adjusted under 35 U.S.C. 154(b) by 0 days.

(21) Appl. No.: 09/068,027

(22) PCT Filed: Aug. 8, 1997

(86) PCT No.: PCT/JP97/02776

§ 371 (c)(1),
(2), (4) Date: Apr. 1, 1998

(87) PCT Pub. No.: WO98/07031

PCT Pub. Date: Feb. 19, 1998

(30) Foreign Application Priority Data

| Aug. 12, 1996 | (JP) | 8-212488 |
| Oct. 4, 1996 | (JP) | 8-264832 |
| Feb. 25, 1997 | (JP) | 9-40814 |
| Mar. 5, 1997 | (JP) | 9-50403 |
| May 22, 1997 | (JP) | 9-132445 |

(51) Int. Cl.⁷ ............... G01N 33/53; G01N 33/543
(52) U.S. Cl. .......... 435/7.1; 435/2; 435/7.23; 435/7.6; 435/7.95; 435/287.1; 435/287.5; 435/287.9; 435/288.1; 435/809; 435/810; 435/969; 435/970; 435/971; 435/973; 435/974; 436/66; 436/518; 436/524; 436/527; 436/547; 436/810; 422/61
(58) Field of Search ............. 435/2, 7.1, 7.23, 435/7.6, 7.95, 287.5, 287.1, 287.9, 288.1, 309.2, 809, 810, 969, 970, 971, 973, 974; 436/66, 500–547, 810; 422/61

(56) References Cited

FOREIGN PATENT DOCUMENTS

| JP | 60-10499 | 1/1985 |
| JP | 62-110153 | 5/1987 |
| JP | 2-196961 | 8/1990 |
| JP | 7-159397 | 6/1995 |
| JP | 3019393 | 10/1995 |

OTHER PUBLICATIONS

Bienvenu (1995), Acute phase cytokines measurement in biological fluids. Comptes Rendus des Seances de la Societe de Biologie et de ses Filiales. 189(4):545–555.*
Bietnvenu et al. (1998). Cytokine assays in human sera and tissues. Toxicology. 129:55–61.*
Schauer et al. (1996). Measurement of intracellular cytokines, Immunology Today. 17(7):305–306.*
Murch et al. (1990). In–vitro production of cytokines in serum. Lancet. 336:687–688.*
McLaughlin et al. (1990). Tumour–necrosis factor in normal plasma. Lancet. 336:1014–1015.*
Thavasu et al. (1992). Measuring cytokine levels in blood—Importance of anticoagulants, processing, and storage conditions. J. Immunol. Meth. 153:115–124.*
Lerous–Roels et al. (1988). Influence of blood–collecting systems on concentrations of tumor necrosis factor in serum and plasma. Clin. Chem. 34(11):2373–2374.*
Riches et al. (1992). Influence of collection and separation of blood samples on plasma IL–1, IL–6 and TNF–a concentrations. J. Immunol. Meth. 153:125–131.*
Redl et al. (1992). Special collection and storage tubes for blood endotoxin and cytokine measurements. Clin. Chem. 38(5):764–765.*

* cited by examiner

Primary Examiner—Christopher L. Chin
(74) Attorney, Agent, or Firm—Rader, Fishman, Grauer PLLC

(57) ABSTRACT

A container for measurement of cell functions, for use in the determination of a physiologically active substance produced by blood cells, is constituted such that an amount of material capable of inducing production of the physiologically active substance, when extracted by collecting water of a volume equal to a liquid volume to be subjected to measurement, is controlled at a level insufficient to induce production of the physiologically active substance from the blood cells. A container for measurement of cell functions in which a material capable of inducing production of a physiologically active substance in blood when contacted with the blood is accommodated in such a condition as being contactable with blood, and in which an amount of the material capable of inducing production of the physiologically active substance in the container before use is limited to a level insufficient to influence a measured value of the physiologically active substance.

12 Claims, 3 Drawing Sheets

CONTAINERS AND KITS FOR THE DETERMINATION OF CELL FUNCTIONS, AND METHOD FOR THE DETERMINATION THEREOF

FIELD OF THE INVENTION

The present invention relates to a container for measurement of cell functions involved in immune and inflammatory reactions, a kit for measurement of the cell functions and a method for measuring the cell functions, and more particularly to a container for measurement of cell functions which is carried out through determination of physiologically active substances, such as cytokines, produced by blood cells including granulocytes, monocytes, macrophages, lymphocytes or the like, for example, kit and method for such a measurement of cell functions.

DESCRIPTION OF PRIOR ART

Leukocytes, such as granulocytes, monocytes, macrophages and lymphocytes, play various rolls in diversified bioprotective reactions including immune and inflammatory reactions in blood or respective organs. It is known that these cells exhibit important functions in a variety of morbidities including infectious diseases; inflammatory diseases such as hepatitis and nephritis; immune.allergic diseases such as rheumatoid arthritis and asthma; and cancer, and the functions of these cells are either suppressed or enhanced as the morbidity varies.

It is also known that a variety of drugs, such as anti-inflammatory drugs, immunosuppressants, immunoenhancers and anticancer drugs, are useful in the therapy of these diseases, wherein the functions of these cells are either suppressed or enhanced concurrently. It is therefore important to examine the functions of these cells whereby the morbidities of various diseases, effects and side-effects of drugs can be identified to determine therapeutic schemes, doses of the drugs and timings of the drug administration.

In view of the above-described reasons, a granulocyte phagocytic activity test, a granulocyte bactericidal activity (active oxygen producing capacity) test, a lymphocyte transformation test and the like have been conventionally conducted at hospital examining rooms or centers in order to measure such cell functions. Also in recent years, a surface antigen test has been carried out which utilizes a flow cytometer and fluorescence-labelled monoclonal antibodies against respective surface antigens of various immunocompetent cells. However, the conventional testing methods have required such specialized techniques as separation and culture of cells, microscopic measurement or the like, to consequently necessitate time-consuming measurements, RI facilities and expensive equipments.

Also, monocytes in blood, as well as macrophages into which the monocytes moved into tissues differentiates and matures, have a wide spectrum of functions, for example, as coming into play in foreign body exclusion through phagocytosis and immune formation through antigen presentation, or as secreting various physiologically active substances, such as cytokine and prostaglandin, to thereby regulate an inflammatory or immune reaction. Like granulocytes and lymphocytes, these monocytes and macrophages play important rolls also in a variety of morbidities. It is therefore very important to identify the functions of these cells. Particularly in infectious diseases, unlike the granulocytes and lymphocytes, the monocytes and macrophages exhibit slight changes in terms of the number of cells and primarily amplify their functions, so that the measurement of changes in cell functions becomes more important ("Macrophages", written by Tohru Tokunaga, Kodansha Scientific, 1st Ed. published in 1986).

Tumor necrosis factor α (hereinafter referred to as TNFα), interleukin-1β (hereinafter referred to as IL-1β), and interleukin-6 (hereinafter referred to as IL-6), all called as monokine, are cytokines which are produced mainly by leukocytes including monocytes and macrophages, among blood cells, and which come into play in various inflammatory and immune reactions.

A variety of methods reported to date examines the above-described cytokine-producing functions of blood or leukocytes separated from blood. For example, in gazettes of Patent Laying-open Nos. Hei 2-196961 and Hei 3-285692, methods are disclosed which react lipopolysaccharide (LPS) or lectin with blood to induce production of cytokines, such as TNFα or IL-1β, which are subsequently quantitatively determined. Also, in gazettes of Patent Laying-open Nos. Hei 6-209992 and Hei 7-67955, methods are disclosed which react blood with polymer materials having a specific surface roughness or chemical structures to induce production of TNFα. Also, in gazettes of Patent Laying-open Nos. Hei 7-299732 and Hei 7-151752, bioreaction tests are disclosed which react blood with polymer materials having a specific surface roughness to determine the amount of produced TNFα or IL-1β. Also, in a gazette of Tokkohyo No. Hei 7-500905, a method is disclosed which measures immunoactivity of a tested substance by determining the production of cytokines, such as TNFα or IL-1β, induced from human peripheral blood leukocytes.

However, the above-described methods for measurement of cell functions which have been conventionally carried out at hospital examining rooms or centers, as well as the methods disclosed in the gazettes of the above-listed laid-open patents, have the following problems. That is, these tests all require specialized operations, such as an operation of collecting blood from an examined human using an injector and thereafter manually transferring the blood to various reactors as by pipetting, cell separation for separating leukocytes and the others, cell culture for the purpose of measuring cell functions or the like. This carries a risk for an examining person to acquire various infectious diseases, such as hepatitis and AIDS, when the person contacts the blood. Also, there is a possibility that various bacteria or dusts are accidentally incorporated into a specimen blood during such operations. There exists another risk of adversely affecting the measurement results when those contaminants or operations physically stimulate the cells in blood without necessity.

Particularly in the conventional methods which employ a specific reactor to collect blood therein and determine the production of cytokines, specifically of TNFα or IL-1β induced from leukocytes, there has existed an occasion that the endotoxin, such as LPS derived from gram-negative bacteria, have been originally incorporated in a blood collecting equipment, such as an injector, or in a reactor. Since even a very slight amount of endotoxin can induce production of TNFα or IL-1β from leukocytes, it was impossible to obtain reliable measurement results when, for example, entry of a slight amount of dusts during a manufacturing process or contamination through employed cleaning water resulted in incorporation of a small amount of endotoxin in the above-described blood collecting equipment or reactor.

In view of the above-described problems, a method for measurement of cell functions is sought which is more simplified in its operations, less risky and more accurate than conventional methods.

In another aspect, anticoagulants have been conventionally utilized when measuring various physiologically active substances in blood, functions of blood cells, surface antigens of blood cells or the like.

However, there exists no general standard for endotoxin contents in anticoagulant, other than a guideline given by "Endotoxin testing method" in the dispensatory of 13th revised Japanese Pharmacopeia, which, for anticoagulants employed as an injection drug, officially sets 5 EU/Kg as a standard for a specification of minimal pyrogenic dose to a rabbit.

Endotoxin is lipopolysaccharide constituting a cell-wall outer membrane of gram-negative bacteria, and a very slight amount thereof suffices to stimulate blood cells, such as leukocytes, to produce physiologically active substances such as a variety of cytokines including TNFα, IL-1β, IL-6, or granulocyte-macrophage colony-stimulating factors. They exhibit various physiological actions such as pyrogenic activity and endotoxin shock (Nippon Igaku-kan "Inflammation and cytokines '87 Inflammation Seminar", p.103–108).

Also, the physiologically active substances, such as the above-described cytokines produced from blood cells, interact with each other in autocrine or paracrine mode to cause further production of histamines, arachidonate metabolites or various cytokines, to modify various functions of blood cells, and to cause quantitative and qualitative changes of blood cell surface antigens.

Accordingly, if anticoagulants are contaminated with endotoxin, and if the contents of such endotoxin are in a sufficient level to cause production of the physiologically active substances, it would become impossible to carry out precise measurements of various physiologically active substances in blood, of functions of blood cells, and of surface antigens of blood cells.

BRIEF SUMMARY OF THE INVENTION

It is an object of the present invention to provide a container, as well as a kit and a method, respectively for measurement of cell functions, which can eliminate the problems imposed upon the conventional methods for measurement of cell functions, which is more simplified in operations and less risky than conventional, and which can measure cell functions at an increased accuracy than conventional.

In accordance with a broad aspect of a first invention, in order to accomplish the above-described object, a container for measurement of cell functions, for use in determining physiologically active substances produced from blood cells, is provided which is characterized in that an amount of material capable of inducing production of the above-described physiologically active substances, when extracted by collecting water of a volume equal to a liquid volume to be subjected to measurement, is at a level insufficient to induce production of the physiologically active substances from the blood cells.

Since, in this container for measurement of cell functions, as described above, the amount of material capable of inducing production of the physiologically active substances, when extracted by collecting water of a volume equal to a liquid volume to be subjected to measurement, is limited to a level insufficient to induce production of the physiologically active substances from the blood cells, that is, the container for measurement of cell functions contains in itself the above-specified limited amount of the material capable of inducing production of the physiologically active substances, the collected blood is scarcely subjected to unnecessary stimulation for a period from collection till measurement so that a long-term preservation thereof is enabled. This allows precise measurement of the physiologically active substances present in the collected blood and enables the use of the container in precisely examining morbidities of patients having various diseases.

Also, the container for measurement of cell functions in accordance with this first invention can be suitably employed to obtain control values, when used in combination with a container for measurement of cell functions in accordance with a below-described second invention.

In the container for measurement of cell functions in accordance with the first invention of the present application, the material capable of inducing production of the above-described physiologically active substances is preferably endotoxin, and its content in the container for measurement of cell functions before use is specified not to exceed 0.5 EU/ml as a concentration in an extracted liquid when extracted by collecting water of a volume equal to a liquid volume to be subjected to measurement.

The second invention of the present application is a container for measurement of cell functions which is characterized in that a material which induces production of physiologically active substances in blood upon contact with the blood, is accommodated therein in such a condition as being contactable with blood, and that the amount, present in the container before use, of the above-described material capable of inducing production of physiologically active substances is limited so as not to adversely affect measured values of the physiologically active substances as described above.

In the container for measurement of cell functions in accordance with the second invention, although the material capable of inducing production of the physiologically active substances in blood is accommodated in such a condition as being contactable with blood, the content of the material capable of inducing production of the physiologically active substances, originally present in the container before accommodation thereof, is limited, as described above, so as not to influence measured values of the physiologically active substances. Accordingly, the production of physiologically active substances can be determined very accurately when the blood is introduced and contacted with the material capable of inducing production of the physiologically active substances to thereby produce the physiologically active substances.

In the container for measurement of cell functions in accordance with the second invention, the material which induces production of the above-described physiologically active substances is preferably endotoxin, and a concentration of endotoxin in a resulting whole liquid when contacted with blood is limited as being in the range of 0.6–100000 EU/ml.

Also, in the container for measurement of cell functions in accordance with the first or second invention, anticoagulants may be further incorporated therein to prevent blood coagulation.

Also, the amount of the material capable of inducing production of physiologically active substances contained in the above-described anticoagulant is preferably at a level insufficient to induce production of the physiologically active substances from blood cells when mixed with blood.

In a particular aspect of the first and second inventions of the present application, the material capable of inducing production of physiologically active substances is endotoxin while the physiologically active substances are cytokines.

At least one species selected from tumor necrosis factor α (TNFα), interleukin-1β (IL-1β) and interleukin-6 (IL-6) can be cited as the above-described cytokines.

Also, an interior of the container for measurement of cell functions, in accordance with the first and second inventions, is preferably vacuumed.

Also, the containers for measurement of cell functions, in accordance with the first and second inventions, can be combined with a reagent capable of quantitating the induced physiologically active substances to thereby constitute a kit for measurement of cell functions. In such an event, an enzyme immunoassay reagent, for example, can be employed as the reagent capable of quantitating the induced physiologically active substances.

A third invention of the present application is a kit for measurement of cell functions. The kit has a first container for measurement of cell functions in which an amount of a material capable of inducing production of the above-described physiologically active substances, when extracted by collecting water which does not contain the material capable of inducing production of physiologically active substances and has such a volume as equal to a liquid volume to be subjected to measurement, is rendered at a level insufficient to induce production of the physiologically active substances from blood cells, and in which anticoagulant may be contained when needed; a second container for measurement of cell functions in which a material capable of inducing production of physiologically active substances in blood when contacted with the blood, as well as anticoagulant, are accommodated in such a condition as to be contactable with blood, and in which the amount, originally present in the container before accommodation thereof, of the above-described material capable of inducing production of physiologically active substances is limited so as not to adversely affect measured values of the physiologically active substances as described above; and a reagent for quantitatively determining the physiologically active substances. That is, the container for measurement of cell functions according to the third invention has a constitution combining the container for measurement of cell functions according to the first invention, the container for measurement of cell functions according to the second invention, and the above-defined reagent for quantification.

In the kit for measurement of cell functions according to the third invention, the above-specified reagent for quantification preferably includes a first enzyme immunoassay reagent for use in determination of the amount of physiologically active substances in blood collected in the first container for measurement of cell functions; and a second enzyme immunoassay reagent which is employed to determine the amount of physiologically active substances produced through a reaction of the material capable of inducing production of the physiologically active substances with the blood collected in the second container for measurement of cell functions, and which is different in sensitivity to the physiologically active substances from the first enzyme immunoassay reagent.

Also, in a particular aspect of the kit for measurement of cell functions according to the third invention, the above-described material which induces production of the physiologically active substances is endotoxin, and a concentration of endotoxin in a resulting whole liquid when contacted with blood is rendered in the range of 0.6–100000 EU/ml.

A fourth invention of the present application is a method for measurement of cell functions which characteristically includes a step of introducing blood into the container according to the second invention for measurement of cell functions and reacting the introduced blood with a material capable of inducing production of physiologically active substances to thereby induce production of the physiologically active substances. In the method for measurement of cell functions according to the fourth invention, the production of above-described physiologically active substances is preferably induced at a temperature of 26–45° C.

Also, a preferred time period during which the production of physiologically active substances is induced is 1–6 hours. Furthermore, in the method for measurement of cell functions according to the fourth invention, the amount of physiologically active substances is determined by reagents capable of quantitating thereof. Also, in a more particular aspect of the method for measurement of cell functions according to the fourth invention, blood is introduced into the first and second containers for measurement of cell functions in the kit for measurement of cell functions to induce production of the physiologically active substances. Again in this case, the production of physiologically active substances is preferably induced at a temperature of 26–45° C., and a preferred time period during which the production of physiologically active substances is induced is 1–6 hours.

DETAILED DESCRIPTION OF THE INVENTION

The present invention will be now explained in detail.

(Container for Measurement of Cell Functions according to The First Invention)

For the container for measurement of cell functions according to the first invention, the amount of material capable of inducing production of the above-described physiologically active substances, when extracted by collecting water devoid of the material capable of inducing production of physiologically active substances and of a volume equal to a liquid volume to be subjected to measurement, is required to be at a level insufficient to induce production of the physiologically active substances from the blood cells.

The extraction method is actually carried out by collecting, into the above container for measurement of cell functions, water devoid of the material capable of inducing production of physiologically active substances and of a volume equal to a liquid volume to be subjected to measurement, and by extracting under agitation for one hour at 37° C.

The above physiologically active substances are preferably cytokines and the material capable of inducing production of physiologically active substances is preferably endotoxin. However, the physiologically active substances are not limited to cytokines, and can be arachidonate metabolites such as prostaglandin, active oxygen species, soluble adhesion factors, soluble receptors, or intragranular enzymes, for example. The type of material capable of inducing production of physiologically active substances can be suitably selected depending upon the type of the physiologically active substances.

In such a case where the material capable of inducing production of physiologically active substances is endotoxin, the endotoxin content in an extracted solution resulting from the above-described extraction is specified not to exceed 0.5 EU/ml (international endotoxin unit). If the above endotoxin content exceeds 0.5 EU/ml, endotoxin is likely to cause a marked induction of cytokines, one class of the physiologically active substances, in the collected blood, and the induced cytokines possibly stimulate various immunocompetent cells to cause changes in functions thereof, consequently making precise measurements of cell functions impossible.

The liquid volume to be subjected to measurement, as described above, refers to a total volume of liquids employed when below-described various measurements are carried out, e.g. a sum of a volume of blood to be measured, a volume of a below-described anticoagulant solution added when needed, a volume of a blood coagulation enhancer solution, and a volume of liquid for dissolving or suspending stimulators.

It should be understood here that the amount in volume of the endotoxin-free water when used in effecting the above-described extraction is not required as being exactly equal to the liquid volume to be subjected to measurement, and it may be below the liquid volume to be subjected to measurement so far as the extraction can be carried out successfully. Even in such a case, the function and effect of the present invention can be obtained, provided that the endotoxin content in the extracted solution does not exceed 0.5 EU/ml.

Although there exists a variety of methods for determining the above endotoxin content, a method referenced in the present specification for determining the endotoxin content is a colorimetry, according to "Endotoxin testing method" in the dispensatory of 13th revised Japanese Pharmacopeia. The colorimetry uses, as an indication, a color produced in a chromophoric synthetic substrate when hydrolyzed, and can be carried out, for example, using a commercially available product ENDOSPECIE (manufactured by Seikagaku Kogyo Co.).

As a method for removing or deactivating endotoxin, various well-known techniques may be employed which include deactivation through heating, acid or alkali treatment; ultrafiltration using a membrane filter; and removal using anionic chitosan resins, polymyxin B specifically bindable to endotoxin, or adsorbents which fixes antibodies against endotoxin. Also, instruments and containers employed for the endotoxin removing operations are subjected to dry heat treatment at 250° C. for an hour or longer, if they are made of glass, or immersed in a 0.2 M aqueous solution of sodium hydroxide and cleaned with endotoxin-free water, if they are made of plastics, to insure complete deactivation of endotoxin prior to use thereof. Also, the endotoxin-free water must be consistently used whenever water is needed, and an operating atmosphere is preferably such an atmosphere that any secondary endotoxin contamination is constrained within a practicable range, as provided by a clean room.

An interior of the container for measurement of cell functions, according to the first invention, is preferably vacuumed. The interior pressure may be reduced to such an extent that atmospheric blood can be suctioned into the container for measurement of cell functions upon communication thereof with the interior of container for measurement of cell functions. The interior pressure can be determined depending upon a blood amount to be suctioned. That is, the larger a target amount of blood to be suctioned is, the higher degree of pressure reduction may be effected.

The shape of container for measurement of cell functions, according to the first invention, is not particularly specified, and may be tubular as exemplified by blood collecting tubes, test tubes and the like, or plate-like as represented by microplates. Preferably, it is suited for vacuum operation.

Illustrative of the type of material for the container for measurement of cell functions are glasses or plastics. Thermoplastic and thermosetting resins can be both employed as the above-described plastics. Cited as examples of the thermoplastic resins are polyethylene, polypropylene, polystyrene, polymethyl methacrylate, polyvinyl chloride, polyethylene terephthalate, styrene-acrylonitrile copolymer, styrene-maleic anhydride copolymer, styrene-acrylate copolymer, styrene-methylmethacrylate copolymer, ethylene-propylene copolymer, ethylene-acrylic acid copolymer, and ethylene-acrylate copolymer. Cited as examples of the thermosetting resins are unsaturated polyester resins, epoxy resins, and epoxy-acrylate resins.

In the event that a tubular part is employed as the container for measurement of cell functions, according to the first invention, a stopper is generally used to maintain the interior of the container at a reduced pressure. Cited as exemplary material types for the stopper are butyl rubbers, chlorinated butyl rubbers, thermoplastic elastomers and the like.

If the tubular part is employed as the container for measurement of cell functions, according to the first invention, the amount of blood to be collected is varied depending upon a volume of the container for measurement of cell functions, but may be generally about 0.5–2 ml in case of using a container having a volume of 4–5 ml.

On the other hand, if a microplate-like part is employed as the container for measurement of cell functions, according to the first invention, the amount of blood to be collected may be about 0.05–2 ml.

If necessary, anticoagulant may be accommodated in the container for measurement of cell functions, according to the first invention, to prevent blood coagulation. The above-described anticoagulant may be present in either liquid or solid form in the container. Cited as the above anticoagulants are heparin compounds, citric acid compounds, oxalic acid compounds and the like. Heparin sodium is more preferable since it does not inhibit biological reactions of cells. When blood is collected in the container, a reduced concentration of heparin sodium in blood possibly causes blood coagulation while an increased concentration thereof is likely to cause unexpected activation or inactivation of cells. Accordingly, a preferred amount of heparin sodium accommodated in the container is 4–50 U/ml.

An exemplary case where the anticoagulant is necessary to be added into the container for measurement of cell functions, according to the first invention, is the case where determination is made as to physiologically active substances produced (released or induced) by reacting cells, such as monocytes, macrophages, lymphocytes, leukocytes or the like, with material capable of inducing production of the physiologically active substances. Also, an exemplary case in which the anticoagulant is not required to be added into the container for measurement of cell functions, according to the first invention, is the case where determination is made as to Regulated on Activation, Normal T Expressed and Secreted (RANTES) released by thrombin stimulating platelets.

Also, when needed, coagulant may be accommodated in the container for measurement of cell functions according to the first invention. Such a case may arise when physiologically active substances are determined through blood coagulation. Thrombin and the like may be cited as examples of such coagulants.

An exemplary method of manufacturing the container for measurement of cell functions, according to the first invention, will be now explained referring to the manufacture of the tubular container. It is manufactured by adding anticoagulant or coagulant, depending upon the need, into a tubular container which has a pressure reducible interior and in which an amount of endotoxin, when extracted by collecting endotoxin-free water of a volume equal to the liquid volume to be subjected to measurement, is rendered at a level insufficient to induce production of physiologically active substances from blood cells; bringing the container into a predetermined vacuum condition; and placing a stopper in the container.

As the above container, a closed-end tubular body, for example, is preferred which is open at one end and closed at the opposite end. An opening portion is preferably configured to be blocked by a stopper body. Also, the container for measurement according to the first invention is preferably manufactured in as clean an atmosphere as possible to avoid infection with endotoxin or various bacteria, and preferably subjected to well-known sterilizing treatment after completion of its manufacture, if possible.

In using the container for measurement of cell functions according to the first invention, the above-specified container for measurement of cell functions is first brought into communication with a blood vessel to allow blood to be suctioned into the above container for measurement of cell functions. In communicating the above blood vessel with the above-specified container for measurement of cell functions, an injector needle may be employed which is utilized for conventional vacuum blood collecting techniques, i.e. a needle (generally called as a multiple injector needle) which has on one side of a needle base a needle portion for thrust into the blood vessel and on another side of the needle base another needle portion for thrust into the stopper in the above-specified container, and in which the above-described needle portion for thrust into the blood vessel is communicated with another needle portion for thrust into the stopper.

The blood obtained through use of the container for measurement of cell functions according to the first invention may be either transferred to another container or subjected to measurement of physiologically active substances through successive use of the container. Also, the obtained blood may be either transferred to another reactor or contacted with material capable of inducing production of physiologically active substances, through successive use of the container as a reactor, for measurement of produced physiologically active substances. In such a case where the container is employed as the reactor for contact with the material capable of inducing production of physiologically active substances, subsequent to blood collection in the container, such a material capable of inducing production of physiologically active substances is introduced into the container.

Determination of physiologically active substances in blood is effected by determining the physiologically active substances in blood collected through use of the container for measurement of cell functions. In this case, the blood collected through use of the container for measurement of cell functions according to the first invention is either transferred to another container or subjected to measurement of physiologically active substances through successive use of the container. In such a case where determination of the physiologically active substances is carried out through successive use of the container, the container, subsequent to blood collection, is generally left to stand or centrifuged to separate hemocyte and plasmas containing physiologically active substances which are quantitatively determined by reagents for respective quantification thereof.

Cited as examples of the above physiologically active substances are TNF-α; interleukins such as IL-1β, IL-4, IL-5 and IL-6; interferons such as INFα, INFβ and INFγ; colony-stimulating factors; chemotactic factors such as IL-8, RANTES and various cytokines; prostaglandins; PGE2 and PGI2; leukotrienes such as LTB4 and LTC4; various chemical mediators such as; nitrogen monoxide, active oxygen, histamines, and platelet-activating factor (PAF). Also cited are adhesion factors such as soluble ICAM1, soluble cytokine receptors such as soluble IL-2 receptor, matrix metallo proteinases, and intracellular granular enzymes such as macrophage-specific elastase.

Cited as an exemplary method of determining the above-described physiologically active substances is an enzyme immunoassay which utilizes monoclonal or polyclonal antibodies against their target physiologically active substances, peroxidases, enzymes such as alkaline phophatases, and chromophoric substrates of respective enzymes.

Cited as exemplary materials capable of inducing production of physiologically active substances are various microorganisms such as endotoxin, BCG dead bacterial and Corynebacteria; synthetic lipid A; pyran copolymer; lectins (such as phytohemagglutinin, concanavalin A, pokeweed mitogen); OK432 (Picibanil); PSK (Krestin); lentinan, zymosan; LPS (lipopolysaccharide); calcium ionophore; phorbol esters; immunoglobulin-fixed carriers; formylpeptides such as formyl-methionyl-leucyl-phenylalanine (FMLP); and various cytokines.

Also usable are specific antigens (for example, house dusts; mite antigens; various pollen antigens such as ragweed pollen extracts, cedar pollen extracts, rice extracts and the like; fungus antigens; parasitic antigens such as ascaris extracts and the like; food antigens such as ovalbumin, wheat, soybean, lobster, crab, meat and the like; and wasp toxin) which are utilized for examination of allergens such as asthma, pollinosis, allergic rhinitis, atopic dermatitis, gastrointestinal allergy, parasitic allergy and the like.

Also cited are materials which fix the above-illustrated materials capable of inducing production of physiologically active substances on various natural or synthetic high molecular weight materials, as by well-known fixation techniques (such as covalent bonding, physical adsorption and the like).

The shape of the above-described materials capable of inducing production of physiologically active substances is not particularly limited, and may be in a liquid or particulate form, for example. Also, they may be fixed on carriers. In case of the liquid form, the above-described materials capable of inducing production of physiologically active substances are generally diluted for use, such as by using, as a diluting liquid, a buffer solution such as phosphate buffer, Hanks' buffer or the like, a normal culture medium such as MEM, RPMI-1640 or the like, a physiological saline (for example, manufactured by Otsuka Seiyaku Co.), or water for injection (for example, manufactured by Otsuka Seiyaku Co.).

The existing form of the above-described material capable of inducing production of physiologically active substances may be either solid or liquid. In the event such a material capable of inducing production of physiologically active substances is water-soluble, it may be coated on an inner wall surface of the container or added to the container before rendered into a powder form. For example, in the case where the material capable of inducing production of physiologically active substances is diluted with water for injection, it is preferred to introduce the material capable of inducing production of physiologically active substances into the container for subsequent dry solidification thereof. In the case where the material capable of inducing production of physiologically active substances is water-insoluble, such a water-insoluble material may preferably be allowed to stay immersed in the above-described diluting liquid, for example, since the possible retention of bubbles on a surface of the material capable of inducing production of physiologically active substances is likely to cause excessive hemolysis when it is brought into contact with blood, such as by tumble mixing, to result in adverse influence on a measurement system.

In the case where the material capable of inducing production of physiologically active substances is fixed to a carrier, if the fixing carrier is a water-soluble material, such a water-soluble material may be coated on an inner wall of the container or added to the container before rendered into a powder form. If the fixing carrier is a water-insoluble material, such a water-insoluble material may preferably be allowed to stay immersed in the above-described diluting liquid, for example, since the possible retention of bubbles on a surface of the water-insoluble material is likely to cause excessive hemolysis when it is brought into contact with blood, such as by tumble mixing, to result in adverse influence on a measurement system.

It is preferred that the amount of the material capable of inducing production of physiologically active substances for addition to the container is properly set to an optimum concentration level, depending on the type of material capable of inducing production of physiologically active substances.

In the method for measurement of cell functions according to the first invention, in the case where another reactor is prepared separately from the container of the first invention, the shape of another reactor is not particularly specified, and may be tubular as exemplified by blood collecting tubes, test tubes and the like, or plate-like as exemplified by microplates and the like. The reactor is preferably adapted such that an amount of endotoxin, when extracted by collecting endotoxin-free water of a volume equal to the liquid volume to be subjected to measurement, is rendered at a level insufficient to induce production of physiologically active substances from blood cells. Here, the meaning of the above-described liquid volume to be subjected to measurement is equivalent to that given above in explaining the container for measurement of cell functions.

In the case where the reactor is prepared separately from the container for measurement of cell functions, as described above, such a reactor can be employed to which the material capable of inducing production of physiologically active substances has been added, and which has been brought into a predetermined vacuum condition. For such a reactor, the communication thereof with the container for measurement of cell functions in which blood has been collected, such as provided by the multiple injector, facilitates transfer of the collected blood to the reactor. Also, the preloading of material capable of inducing production of physiologically active substances simplifies a reaction process.

In the above case, it is preferred that the amount of material capable of inducing production of physiologically active substances for addition to the reactor is properly set to an optimum concentration level, depending on the type of material capable of inducing production of physiologically active substances. One exemplary method of manufacturing this reactor is cited below. The material capable of inducing production of physiologically active substances and, if necessary, anticoagulant are added to a tubular container which has a pressure reducible interior. Then, the reactor is brought into a predetermined vacuum condition before the stopper is placed therein. The reactor for use in the present invention is preferably manufactured in as clean an atmosphere as possible to avoid infection with endotoxin or various bacteria, and is preferably subjected to well-known sterilizing treatment after completion of its manufacture, if possible.

As the above-described reactor, a closed-end tubular body, for example, is preferred which is open at one end and closed at the opposite end. The opening portion is preferably configured to be successfully blocked by a stopper body. The above closed-end tubular body is preferably a test tube-like body suited for centrifugal operation, subsequent to the reaction, for measurement of the above-described material capable of inducing production of physiologically active substances, and its preferred size is 5–30 mm in outer diameter and 20–150 mm in height.

(Container for Measurement of Cell Functions according to The Second Invention)

The container for measurement of cell functions according to the second invention is characterized in that a material, capable of inducing production of physiologically active substances in blood when it contacts the blood, is accommodated therein in such a condition as being contactable with blood. This material capable of inducing production of physiologically active substances may also be hereinafter referred to as a physiologically active substance-inducing material. Cited as the physiologically active substances can be those listed in the explanation of the first invention, and preferred are cytokines.

Also, a preferred physiologically active substance-inducing material is endotoxin. Endotoxin acts on monocytes and macrophages in blood to promote activation of these cells and induce production of cytokines. Cited as the above endotoxin is endotoxin consisting of cell-wall polysaccharide (LPS) derived from microorganisms, for example. Also, materials can be employed which fixed endotoxin in various natural or synthetic high molecular weight materials by a fixation technique.

The use amount of endotoxin is chosen such that a concentration of endotoxin in a whole liquid (a sum of blood, an anticoagulant solution, an endotoxin dissolved solution and the others) when contacted with blood preferably falls within 0.6–100000 EU/ml, more preferably within 0.8–80000 EU/ml. As the concentration falls below 0.6 EU/ml, the amount of induced TNF$\alpha$, IL-1$\beta$ and IL-6 possibly becomes excessively small. As the concentration goes beyond 100000 EU/ml, the amount of induced TNF$\alpha$, IL-1$\beta$ and IL-6 possibly becomes excessively small. This also adds to the cost.

In the container for measurement of cell functions according to the second invention, the above-described physiologically active substance-inducing material is rendered in such a condition as to be contactable with blood within the container. Such a condition as to be contactable with blood is, for example, where the physiologically active substance-inducing material is accommodated in the container.

The general shape of the physiologically active substance-inducing material is either a powder form or a liquid form taken when the inducing material is dissolved in a solvent such as water. The condition of the inducing material present in the container may be a solid, gel or liquid form. In the case of water-soluble inducing material, it may be dissolved in a suitable solvent for subsequent coating thereof on an inner wall surface of the container or addition to the container before brought into a powder form.

Any of buffers such as phosphate buffer, Hanks' buffer and the like, and normal media such as MEM, RPM-1640 and the like can be utilized as the above-described solvent, so far as it is a physiological buffer. Also, a commercially available water for injection (LPS-free water, manufactured by Otsuka Seiyaku Co.) as well as a physiological saline (manufactured by Otsuka Seiyaku Co.) can be utilized. Besides endotoxin, various materials illustrated in the explanation of the first invention can also be utilized as the physiologically active substance-inducing materials.

In addition, the high molecular weight materials disclosed in a gazette of Patent Laying-open No. Hei 6-209992 which have a surface roughness measuring 0.2 μm–10 μm of a centerline average roughness Ra value and 5 μm–200 μm of a mean spacing from peaks to valleys, the high molecular weight materials disclosed in a gazette of Patent Laying-open No. Hei 7-67955 which have at least one chemical structure selected from the group consisting of a hydroxyl group, an amido skeleton, and an ester skeleton within a molecule, or high molecular weight materials having a cationic functional group can be also used as the above-described physiologically active substance-inducing materials.

Also, among the above-described physiologically active substance-inducing materials, phytohemagglutinin is a preferred cytokine-inducing material. Phytohemagglutinin is tetrameric lectin, and its constitutive subunits include E subunit having hemagglutinative activity and L subunit having leukoagglutinative activity. Phytohemagglutinin-P (PHA-P) which is a tetramer consisting of E subunit and L subunit, and phytohemagglutinin-L (PHA-L) which is a tetramer of L subunit, are preferred as usable phytohemagglutinins. PHA-P and PHA-L may be used solely or in combination thereof.

Also, when comparison is made between PHA-P and PHA-L as to their abilities to induce production of cytokines, with their use amounts being made equal, the induced amount exhibits about 10 times as high by PHA-L as by PHA-P. Accordingly, PHA-L is particularly preferred as the cytokine-inducing material. In case of PHA-L, a concentration of phytohemagglutinin-L in a whole liquid (a sum of blood, an anticoagulant solution, a PHA-L dissolved solution and the others), when brought into contact with blood, is preferably rendered to fall within 0.1–100 μg/ml, and more preferably rendered to fall within 0.5–50 μg/ml. As the above concentration falls below 0.1 μg/ml, the amount of induced TNFα and IL-1β possibly becomes excessively small, and as the concentration goes beyond 50 μg/ml, the amount of induced TNFα and IL-1β possibly becomes excessively small, which consequently adds to the cost.

Also, the above-described cytokine-inducing materials, other than endotoxin, are preferably those containing substantially no endotoxin, so-called endotoxin-free materials.

Also, the amount of physiologically active substance-inducing material incorporated in the container for use in the second invention must be regulated prior to use so as not to influence measured values of the above inductively produced physiologically active substances. As apparent from the below-described EXAMPLES, as the content of endotoxin such as LPS increases, a marked induction of cytokines is caused. Accordingly, in order to precisely perform measurement of cell functions according to the second invention, the content of physiologically active substance-inducing material must be not greater than the level insufficient to induce cytokines.

The above-described endotoxin content, when endotoxin-free water of a volume equal to a liquid volume to be subjected to measurement is collected in the container for subsequent extraction under agitation at 37° C. for one hour, in the same manner as in the first invention, is preferably rendered not greater than 0.5 EU (international endotoxin unit)/ml, as a concentration in the extracted solution.

Various techniques described in the explanation of the first invention can be employed as methods of removing or deactivating endotoxin.

Also, since the container for measurement of cell functions, according the second invention, is employed for measuring functions of cells present in blood, anticoagulant may preferably be accommodated in the above container to prevent blood coagulation.

The existing form, type and loading of the above anticoagulant are the same as in the case of the container for measurement of cell functions according to the first invention. Also, concerning the material types of the container for measurement of cell functions according to the present invention, those can be employed which are the same as of the container for measurement of cell function according to the first invention.

Furthermore, in the container for measurement of cell functions according to the second invention, an interior thereof is preferably vacuumed, thereby enabling ready suction of blood into the interior of the container for measurement of cell functions according to the second invention. In such a case, the use of a stopper is desired to maintain the interior at a reduced pressure, as similar to the case of the container for measurement of cell functions according to the first invention, and various materials illustrated in the explanation of the container for measurement of cell functions according to the first invention can be exemplified as material types of the stopper.

The amount of blood collected in measuring cell functions using the container for measurement of cell function according to the second invention is dependent on a volume of the container for measurement of cell functions, but about 0.5–2 ml is sufficient when the employed container for measurement of cell functions has a volume of 4–5 ml.

Cited as an exemplary method of manufacturing the container for measurement of cell functions according to the second invention is a method wherein the above-described physiologically active substance-inducing material, as well as anticoagulant, are added to a container which has a pressure reducible interior, the container is brought into a predetermined vacuum condition, and the stopper is placed in the container.

As the above-described container, a closed-end tubular body, for example, is preferred which is open at one end and closed at the opposite end. The opening portion is preferably configured to be blocked by a stopper body. More preferred as the above closed-end tubular body is the one suited for centrifugal operation performed subsequent to the reaction of inducing cytokines and for determining the amount of induced cytokines, and its preferred size is 5–30 mm in outer diameter and about 20–150 mm in height.

Also, the container for measurement of cell functions according to the first invention is preferably manufactured in as clean an atmosphere as possible to avoid infection with endotoxin or various bacteria, and is preferably subjected to well-known sterilizing treatment after completion of its manufacture, if possible.

A method of measuring cell functions will now be explained utilizing the container for measurement of cell functions in accordance with the second invention.

First, the above-described container for measurement of cell functions is brought into communication with a blood vessel or a blood collecting container so that a specimen blood is suctioned into the container for measurement of cell functions. Moderate shaking is then applied to the container for measurement of cell functions to contact the blood cells with the above-described physiologically active substance-inducing material for subsequent inductive reaction. As the reaction ceases, the container is either left to stand or centrifuged to separate hemocyte and plasmas, and thereafter the cytokines in the plasmas are quantitatively determined by reagents capable of quantitating respective cytokines.

The above-described technique to communicate the first container for measurement of cell functions with the blood collecting container can be utilized to communicate the above-described blood collecting container with the above-described container for measurement of cell functions.

If the temperature at which the blood is reacted with the above cytokine-inducing material becomes lower, the metabolic activity of cells is possibly lowered to result in an excessively decreased amount of cytokines induced, and if it is elevated, the cell damage is possibly caused to result in an excessively decreased amount of cytokines induced. Accordingly, it is controlled preferably at 26–45° C., more preferably at 30–42° C.

If the time period during which the blood is reacted with the above cytokine-inducing material is shortened, the amount of cytokines induced possibly becomes excessively small, and if it is excessively prolonged, the production of measurement results is delayed. Also, the amount of cytokines induced shows a trend of gradually decreasing from a peak which takes place in about 4 hours. The preferred time period is thus 1–6 hours, more preferably 2–4 hours.

In the method of measuring cell functions utilizing the container for measurement of cell functions according to the second invention, it is most preferred that a whole blood collected in the container for measurement of cell functions is cultured at 30–40° C. for 2–6 hours to induce cytokines.

The enzyme immunoassay described in the explanation of the container for measurement of cell functions according to the first invention can be utilized to quantitatively determine induced cytokines.

One embodiment of a technique to measure cell functions using the container for measurement of cell functions according to the second invention will be now explained in detail. First, the above-described cytokine-inducing material is reacted with blood in the above-described container for measurement of cell functions to induce cytokines. As the induction completes, the container for measurement of cell functions is centrifuged at 1200 G to separate hemocyte components and plasma components. Next, the separated plasmas are added using a pipette into a well of a microplate on which monoclonal anti-cytokine antibodies have been fixed for subsequent reaction at 37° C. for 2 hours. Then, the plasma solution after reaction was removed by means of suction removal or the like, and in addition, the well is washed with a neutral pH cleaning buffer containing a nonionic surfactant, such as Tween 20, to further remove unreacted components. Horseradish peroxidases-fixed polyclonal anti-cytokine antibodies are then pipette added to the well for reaction at 37° C. for 1 hour. The well is then washed with the above cleaning buffer to remove unreacted horseradish peroxidases, and thereafter a substrate solution containing hydrogen peroxide and tetramethylbenzidine is added for reaction for 5~10 minutes. An 1 M solution of sulfuric acid is added to discontinue the reaction before determining a color produced in the substrate due to an enzyme reaction from absorbance at 450 nm. The determined value is evaluated against a calibration curve prepared by using cytokines of known concentration to determine the level of cytokines induced.

(Kit for Measurement of Cell Functions)

Each of the containers for measurement of cell functions according to the first and second inventions can be combined with a reagent capable of quantitating physiologically active substances, such as an enzyme immunoassay reagent, to provide a usable kit for measurement of cell functions. That is, a kit for measurement of cell functions can be provided which has the container for measurement of cell functions according to the first invention and the reagent capable of quantitatively determining induced physiologically active substances. In addition, a kit for measurement of cell functions can also be provided which has the container for measurement of cell functions according to the second invention and the reagent capable of quantitatively determining physiologically active substances induced.

The technique referred to above as one embodiment of measuring cell functions with the use of the container for measurement of cell functions according to the second invention can be similarly employed when using the above-described kits for measurement of cell functions, for example.

(Preferred Anticoagulants)

In the present invention, the amount of material capable of inducing production of physiologically active substances contained in the above-described anticoagulant is desirably controlled at a level insufficient to produce the physiologically active substances from blood cells when mixed with blood. That is, the reduction in amount of the physiologically active substances originally contained in the anticoagulant effectively restrains the occurrence of unnecessary stimulation given to the collected blood prior to assaying. The production of physiologically active substances in the collected blood due to the action of the anticoagulant is thus regulated, so that the determination of various physiologically active substances, measurement of cell functions, and determination of surface antigens of blood cells can be carried out more precisely. Also, a specimen of blood can be preserved for a prolonged period from collection till assaying.

Again in such a case, the physiologically active substance-inducing materials may be those described above, and preferred one is endotoxin. The increased content of endotoxin causes production of the above-listed cytokines, such as $TNF\alpha$, $IL-1\beta$, $IL-6$ and the others, to interfere with a precise measurement. Accordingly, the endotoxin content in the anticoagulant is desirably regulated to a level insufficient to produce cytokines, as physiologically active substances, in collected blood.

As will become apparent from Examples described hereinafter, the production of cytokines, such as $TNF\alpha$, $IL-1\beta$, $IL-6$ and the others, is possibly induced if the endotoxin content in anticoagulant goes beyond 0.5 EU/ml in reactive blood. It is accordingly desired to regulate the endotoxin content in anticoagulant so that the endotoxin content in a reactive liquid does not exceed 0.5 EU/ml.

The amount of the above-described anticoagulant is dependent upon the blood amount to be collected, but is generally 0.5–5 mg/ml in blood, if sodium ethylenediamine tetraacetate is used, 3–5 weight % in blood, if sodium citrate is used, and 4–50 U/ml in blood, if heparin sodium is used.

Accordingly, it is preferred in the present invention that the endotoxin content in anticoagulant may be suitably selected depending on the amounts respectively of anticoagulant and collected blood, such that the endotoxin content in blood collected results in a level not exceeding 0.5 EU/ml.

For example, when 1 ml of blood is collected for examination, heparin sodium, if selected for use, is added generally in an amount of 4–50 U/ml, and accordingly the preferred endotoxin content thereof is not greater than 00.125 EU/heparin unit, more preferably not greater than 0.01 EU/heparin unit.

The variety of techniques described in the explanation of the first invention for removing or deactivating endotoxin, for example, can be employed to manufacture anticoagulant containing a reduced amount of endotoxin.

However, the inactivation of endotoxin with heat, acid or alkali treatment sometimes accompanies deactivation of a certain anticoagulant itself. Accordingly, the ultrafiltration using a membrane or the removal using an adsorbent is preferred.

(Measurement of Cell Functions)

The term "measurement of cell functions" as used in the present invention is intended to include a method of directly measuring functions of a blood cell which may be classified into an erythrocyte, a platelet and a leukocyte, a method of evaluating cell functions through determination of physiologically active substances, and measurement of blood cell surface antigens.

The measurement of functions of the blood cell which is classified into the above-mentioned erythrocyte, platelet and leukocyte include hemagglutination, platelet agglutination, leukocyte migration, leukocyte migration inhibition test, leukocyte nitroblue tetrazolium reduction, leukocyte phagocytic activity, lymphocyte transformation, lymphocyte cytotoxic test, antibody-dependent cell-mediated cytotoxic activity test, cytokines-producing capacity, histamine release test and the like, for example.

Also, the measurement of cell surface antigens refers to measurement of cell surface antigens through a rosette formation test or flow cytometry, and includes measurement of Fc receptors and various CD antigens, for example.

(Kit for Measurement of Cell Functions according to The Third Invention)

The kit for measurement of cell functions according to the third invention has the above-described container for measurement of cell functions according to the first invention, the container for measurement of cell functions according to the second invention and the reagent.

The details of usable containers for measurement of cell functions according to the first and second inventions are hereinbefore described.

In order to measure the cell functions using the kit for measurement of cell functions according to the third invention, the container for measurement of cell functions according to the second invention is communicated with a blood collecting container, a specimen of blood is introduced into the container for measurement of cell functions according to the second invention, and then the container for measurement of cell functions according to the second invention is shaken to react the blood cells with the physiologically active substance-inducing material.

Also, in order to obtain a control value, the blood collecting container is communicated with the container for measurement of cell functions according to the first invention to introduce the specimen of blood into the container for measurement of cell functions according to the first invention.

Next, the containers for measurement of cell functions according to the first and second inventions, into which blood has been introduced in such a manner as described above, are either left to stand or centrifuged to separate hemocyte and plasmas, and the physiologically active substances in plasmas in respective containers for measurement of cell functions according to the first and second inventions are separately quantitatively determined by the use of the first and second enzyme immunoassay reagents having respective measurement sensitivities different from each other.

The communication of the blood collecting container with the respective containers for measurement of cell functions according to the first and second inventions can be achieved using the above-described technique.

As the reaction temperature of the blood and endotoxin in the container for measurement of cell functions according to the second invention decreases, reduced metabolic activity of cells, as well as reduced induction of cytokines, result. As it increases, cell injury and reduced induction of cytokines result. Accordingly, it is preferably 26–45° C., more preferably 30–42° C.

In view of the efficient production of cytokines and prevention of excessive hemolysis, the reaction period of the blood and endotoxin is preferably 1–12 hours, more preferably 2–6 hours.

In the kit for measurement of cell functions according to the present invention, the physiologically active substances in blood collected in the container for measurement of cell functions according to the second invention, that is, the physiologically active substances produced in blood due to its reaction with the physiologically active substance-inducing material is quantitatively determined by the second enzyme immunoassay reagent. The physiologically active substances produced in blood due not to its reaction with the physiologically active substance-inducing material is quantitatively determined by the first enzyme immunoassay reagent. The resulting differential allows determination of the exact production of physiologically active substances induced by the physiologically active substance-inducing material.

Generally, the amount of cytokines in blood (the amount of cytokines in blood collected in the first container for measurement of cell functions) prior to its reaction with endotoxin is several pg/ml—several hundreds pg/ml, and the amount of cytokines in blood after its reaction with endotoxin ranges from several hundreds pg/ml to several thousands pg/ml or higher.

However, there exists no such a reagent having a measurement sensitivity sufficient to quantitate cytokines over a wide range of several pg/ml—several thousands pg/ml. Accordingly, for determination of cytokines in an amount of 1,000 pg/ml or higher, plasmas have been diluted with a suitable diluting solution. However, the diluting operation of plasmas is complicated, separately requires the diluting solution and a dilution container, and accordingly leads to a markedly prolonged measurement period. Also, the measured value is obtained by multiplying the degrees of dilution, which has brought about a problem of lowering accuracy of the measured value.

In contrast, in accordance with the third invention, the amount of cytokines in blood (i.e., the amount of cytokines in blood collected in the first container for measurement of cell functions) prior to its reaction with endotoxin can be determined by the first enzyme immunoassay reagent of high sensitivity, such as of a measurement sensitivity of 10–1,000 pg/ml, while the amount of cytokines in blood (i.e., the amount of cytokines in blood collected in the second container for measurement of cell functions) after its reaction with endotoxin can be determined by the second enzyme immunoassay reagent of low sensitivity, such as of a measurement sensitivity of 500– about 10,000 pg/ml. The above-described, complicated diluting operation can thus be eliminated.

Also, if the above-described cytokine consists of TNFα or IL-β, the preferred sensitivity of the first enzyme immunoassay reagent is 10–500 pg/ml and that of the second enzyme immunoassay reagent is 500–10,000 pg/ml, if LI-6, the preferred sensitivity of the first enzyme immunoassay reagent is 10–1,000 pg/ml and that of the second enzyme immunoassay reagent is 1,000–20,000 pg/ml.

Each of the above-described first and second enzyme immunoassay reagents is comprised of either monoclonal or polyclonal antibody against its target cytokines, enzymes such as peroxidases or alkaline phosphatases, and chromophoric substrates in respective enzymes. The sandwich enzyme immunoassay, wherein the monoclonal antibody against its target cytokines is prefixed on a solid surface as of a microplate, is preferred since it does not require the fixation prior to measurement and is excellent in reproducibility.

A technique of fixing the monoclonal antibodies on the solid surfaces may be arbitrarily chosen from the known physical adsorption or chemical bonding technique, but the physical adsorption is preferred for its simplified operation.

The preparation of the first and second enzyme immunoassay reagents having different sensitivities can be accomplished by selectively adjusting concentrations respectively of monoclonal or polyclonal antibodies against their target cytokines, enzymes such as peroxidases or alkaline phosphatases, and chromophoric substrates in respective enzymes.

For example, in the case where the sandwich enzyme immunoassay is employed, the amount of the above-mentioned monoclonal antibody against its target cytokines for fixation on the microplate may be adjusted, so that the first and second enzyme immunoassay re agents can be prepared which have different sensitivities. That is, the amount of target cytokines bindable to the monoclonal antibody changes depending on the amount of monoclonal antibody fixed on the microplate surface, which enables preparation of reagents having different measurement sensitivities.

Such different measurement sensitivities can also be accomplished by preparing different concentrations of either enzyme-labelled monoclonal antibody or enzyme-labelled polyclonal antibody against its target cytokines, which differ from the target cytokines of the fixed monoclonal antibody, as a reagent for detecting cytokines bound to the fixed monoclonal antibody.

There also is a method in which a specific binding mode such as avidin-biotin is incorporated in the above-described enzyme immunoassay system, e.g. a method in which biotin-labelled antibody or/and avidin-labelled enzyme is used as an alternative to enzyme-labelled antibody against its target cytokines which differ from the target cytokines of the fixed monoclonal antibody.

An exemplary preparation of the monoclonal antibody-fixed microplates will be now explained which can be employed for the present first and second enzyme immunoassay reagents having different measurement sensitivities.

First, the specific monoclonal antibody against its target cytokines is such dissolved in a buffer solution, such as phosphate buffer, as to prepare two types of dilute solutions of concentration levels different from each other (each concentration level prepared is suitably selected depending upon the magnitude of binding constant of the employed monoclonal antibody and its target cytokines).

Each of the two types of monoclonal antibody dissolved solutions is added in a given amount to a microplate for incubation at 2–8° C. for a day and a night. Subsequent washing with a neutral pH cleaning buffer containing a nonionic surfactant such as Tween 20, a given amount of 1–4 weight % bovine serum albumin dissolved phosphate buffer solution is added to the microplate for incubation at 37° C. for 2 hours. After removal of liquids from the microplate, it is dried at room temperature.

One embodiment of measuring cell function using the kit for measurement of cell functions according to the third invention will be now explained in detail.

First, blood is introduced into each of the first and second containers for measurement of cell functions for incubation at 37° C. for 4 hours. Each container is centrifuged at 1600 G to allow hemocyte and plasmas to separate. Then, the separated plasmas are added to wells of respective microplates to which the monoclonal antibody against its target cytokines has been fixed in two different concentration levels, which have been blocked at unadsorbed cites by the bovine serum albumins, and which have been dried, for reaction at 37° C. for 2 hours. Next, the plasma solution after reaction is discarded by means of suction removal and the like, followed by washing the wells with the neutral pH cleaning buffer containing a nonionic surfactant such as Tween 20 to further remove unreacted components. Thereafter, the horseradish peroxidase-fixed polyclonal antibody against the above-specified cytokines is added to the wells for reaction at. 37° C. for 1 hour. In order to remove the unreacted portion of horseradish peroxidase-fixed polyclonal antibody, the wells are washed with the aforementioned cleaning buffer, and thereafter a substrate solution containing hydrogen peroxide and tetramethyl-benzidine is added to the wells for reaction for 5–10 minutes. A 2 M solution of sulfuric acid is then added, the reaction is terminated, and a color produced in the substrate as a result of the enzyme reaction is measured from absorbance at 450 nm. The comparison of the measured value with a calibration curve prepared against the above-specified cytokines of a known concentration quantitatively determines the cytokines in blood as treated in each of the first and second containers for measurement of cell functions.

(Method for Measurement of Cell Functions according to The Fourth Invention)

The method for measurement of cell functions according to the fourth invention is characterized by introducing blood into the first or second container for measurement of cell functions and measuring the cell functions. In this case, the container for measurement of cell functions preferably accommodates, in advance, the above-specified anticoagulant which contains endotoxin in such a limited concentration as not to induce blood cells to produce physiologically active substances when mixed with blood.

One embodiment of the method for measurement of cell functions according to the fourth invention is explained below.

The anticoagulant, e.g. heparin sodium is accommodated in an injector having a blood-collecting needle in a typical amount of 10 U/ml per blood to be collected, before blood is collected from an examined person into the injector. Alternatively, the anticoagulant may be accommodated in a vacuum blood-collecting tube in the same amount as above before effecting collection of blood. Next, this blood is centrifuged at 1600 G, and the amount of TNFα, as illustrative of the physiologically active substance produced from blood cells, in plasma is determined using the enzyme immunoassay.

Also, in a more particular aspect of the method for measurement of cell functions according to the fourth invention, the container for measurement of cell functions according to the second invention is utilized. In such a case, the physiologically active substance-inducing material is arranged within the container so as to be contactable with blood. Accordingly, if brought into contact with blood, the physiologically active substance-inducing material reacts with blood to induce production of the physiological active substances, as above-described in the explanation of the container for measurement of cell functions according to the second invention. The physiological active substances induced can be determined using the aforementioned techniques.

A preferred temperature at which the physiologically active substances are induced is in the range of 26–45° C., and a preferred time period of inducing the physiologically active substances is 1–6 hours.

Also, the physiologically active substances induced can be quantitatively determined by reagents capable of quantitating thereof, e.g. enzyme immunoassay reagents.

DESCRIPTION OF THE PREFERRED EMBODIMENTS

Figure 1:
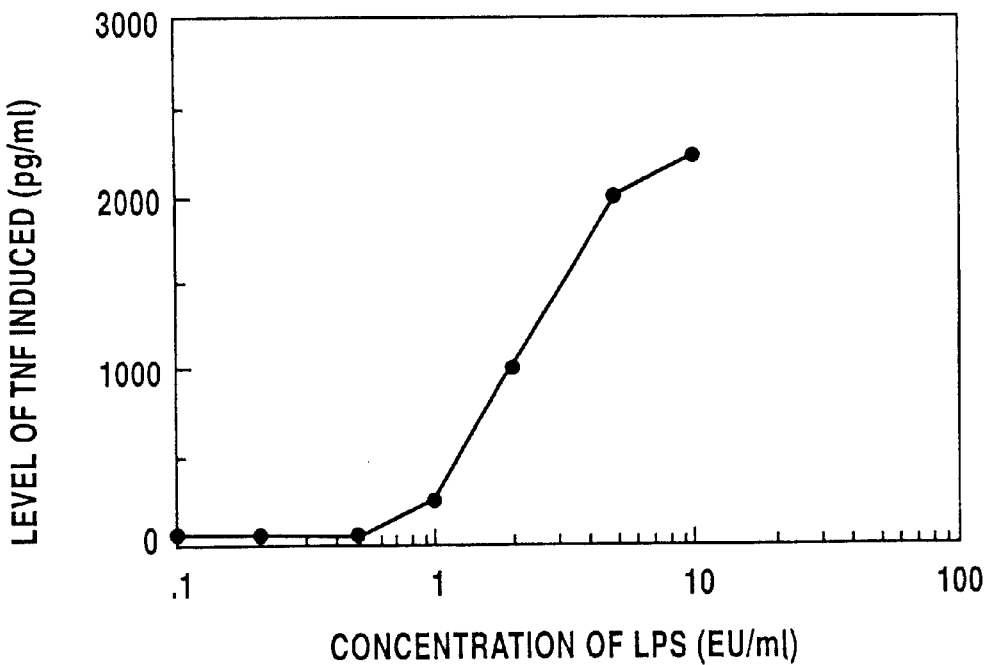
FIG. 1 is a graph showing measurement results obtained in Examples 1–4 and Comparative Examples 2–4, wherein the abscissa indicates the concentration of LPS and the ordinate indicates the amount of TNFα induced.

The present invention will be now explained in detail by citing Examples of the present invention and Comparative Examples. It should be understood that the present invention is not limited to the Examples which follow.

Examples 1–4, Comparative Examples 1–4

(1) Method for Manufacturing A Container for Measurement of Cell Functions:

A 4 ml blood-collecting tube (12.6×75 mm in diameter) made of polyethylene terephthalate was well washed 10 times with 4 ml of endotoxin-free water (manufactured by Otsuka Seiyaku Co.). 0.05 ml of a physiological saline for injection (manufactured by Otsuka Seiyaku Co.) containing heparin sodium (manufactured by Novo.Nordisk A/S Co., product name: Novo.Heparin # 1000) in concentration of 200 U/ml was added to the blood-collecting tube.

*E. coli* UKT-B derived endotoxin (standard product Lot. 8920 of Japanese pharmacopeia) was dissolved in a physiological saline for injection (manufactured by Otsuka Seiyaku Co.) for subsequent stepwise dilution. As each dilution step completed, 0.05 ml of the resulting endotoxin dissolved physiological sline is added to every two of the heparin incorporated blood-collecting tube, so that the blood-collecting tubes were prepared which respectively contained endotoxin in concentrations of 0 EU/ml (Comparative Example 1), 1 EU/ml (Comparative Example 2), 2 EU/ml (Comparative Example 3), 5 EU/ml (Comparative Example 4), 10 EU/ml (Example 1), 20 EU/ml (Example 2), 50 EU/ml (Example 3) and 100 EU/ml (Example ) per a whole solution summing the heparin dissolved physiological saline and the endotoxin dissolved physiological saline.

Next, a butyl rubber-made stopper, which was configured to fit into the tube and had been previously washed with an endotoxin-free water (manufactured by Otsuka Seiyaku Co.), was lightly placed at an opening of each blood-collecting tube so as not to tightly close the opening. Then, every blood-collecting tube was placed within a vacuum container. When an interior of the container was gradually reduced to a pressure of 570 mmHg, the opening of each blood-collecting tube was tightly closed by the stopper. The blood-collecting tubes thus prepared were employed as the containers for measurement of cell functions in Examples 1–4 and Comparative Examples 1–4, respectively.

(2) Determination of Endotoxin Contents in The Blood-Collecting Tubes (Containers):

The endotoxin-free water (manufactured by Otsuka Seiyaku Co.) was introduced into an injector with a needle. The needle of injector was thrust into the butyl rubber-made stopper, as placed on each of the four vacuumed blood-collecting tubes which were obtained in the above (1) as containing heparin solely, to inject 0.9 ml of the endotoxin-free water (manufactured by Otsuka Seiyaku Co.) into each of the blood-collecting tubes, followed by agitation at 37° C. for 1 hour to extract endotoxin. Then, the endotoxin content in the extracted liquid was determined through a synthesized chromophoric substrate technique using a kit for the determination of endotoxin, ENDOSPECIE ES6 (product name) manufactured by Seikagaku Kogyo Co.

The results indicated the endotoxin content in the extracted liquid as being not greater than 0.05 EU/ml for each of the tested four blood-collecting tubes.

(3) Method for Determining TNFα, IL-1β and IL-6 Inducing Activities:

Using an injector with a needle, heparinized blood was collected from a usually healthy volunteer. The needle of injector was thrust into the butyl rubber-made stopper, as placed on each of the vacuumed blood-collecting tubes which were obtained in the above (1) as containing endotoxin in various concentrations, to inject 0.9 ml of the collected specimen blood into each of the blood-collecting tubes. Next, each of the blood-collecting tubes was mounted to a rocker platform for tumble mixing in a thermostatic chamber preheated to a temperature of 37° C. for subsequent tumble mixing for 4 hours. As the intimate mixing was completed, each blood-collecting tube was centrifuged at 1600 G at 4° C. for 10 minutes to collect a supernatant plasma. The collected plasma was determined for contents of cytokines (pg/ml), i.e. respective contents of TNFα, IL-1β and IL-6, using an enzyme immunoassay kit which utilized respective monoclonal antibodies against them.

Figure 2:
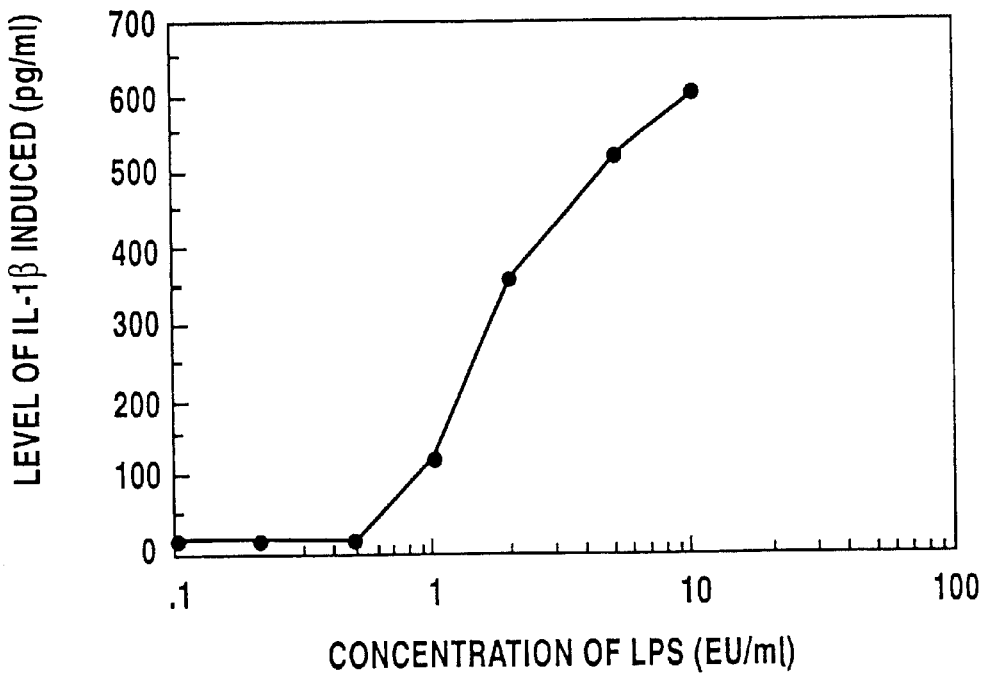
FIG. 2 is a graph showing measurement results obtained in Examples 1–4 and Comparative Examples 2–4, wherein the abscissa indicates the concentration of LPS and the ordinate indicates the amount of IL-1β induced.
Figure 3:
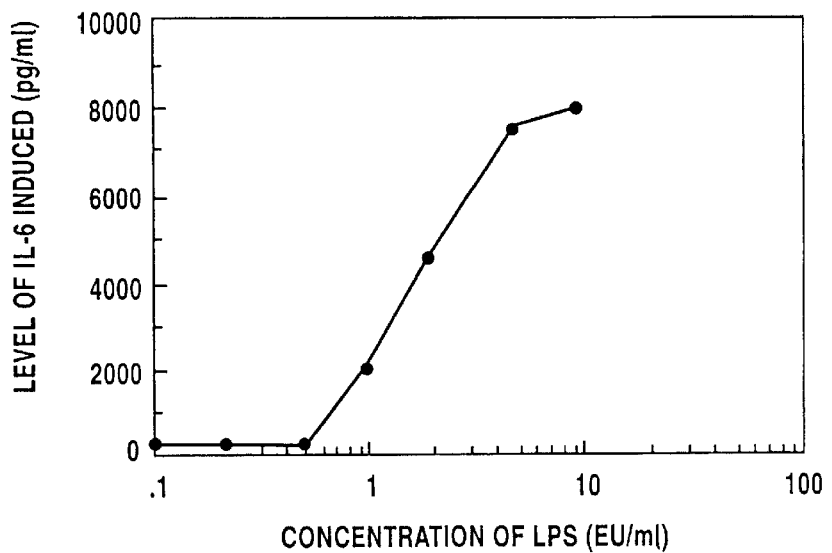
FIG. 3 is a graph showing measurement results obtained in Examples 1–4 and Comparative Examples 2–4, wherein the abscissa indicates the concentration of LPS and the ordinate indicates the amount of IL-6 induced.

PREDICTA Human TNF-α ELISA KIT (limit of detection: 35 pg/ml), PREDICTA Human IL-1β ELISA KIT (limit of detection: 15 pg/ml) and PREDICTA Human IL-6 ELISA KIT (limit of detection: 35 pg/ml) were employed (all manufactured by Genzyme Inc.) to determine the productions in weight of TNFα, IL-1β and IL-6, respectively. The determination was effected using n=3 for each. The results are shown in FIGS. 1–3.

In all Figures, the unit EU/ml used for the LPS concentration on the abscissa indicates the endotoxin concentration in a whole solution when in contact with blood, and the induced amount (pg/ml) on the ordinate indicates an average value of the values obtained from the two blood-collecting tubes for each cytokine concentration in plasma. As apparent from the results, endotoxin at a concentration of 0.6 EU/ml or higher clearly induces productions of TNFα, IL-1β and IL-6. The results from the case where the endotoxin concentration was 0 EU/ml (Comparative Example 1) are not shown in FIGS. 1–3, since in this case, the concentration of each cytokine produced was below the limit of detection in the determination thereof.

Examples 5–10

(1) Method for Manufacturing A Container for Measurement of Cell Functions:

A 4 ml blood-collecting tube (12.6×75 mm in diameter) made of polyethylene terephthalate was well washed 10 times with 4 ml of endotoxin-free water (manufactured by Otsuka Seiyaku Co.). 0.05 ml of a physiological saline for injection (manufactured by Otsuka Seiyaku Co.) containing heparin sodium (manufactured by Novo.Nordisk A/S Co., product name: Novo.Heparin # 1000) in a concentration of 200 U/ml was added to the tube.

E. coli 055:B5 derived endotoxin (manufactured by LBL corp.) was dissolved in a physiological saline for injection (manufactured by Otsuka Seiyaku Co.) for subsequent stepwise dilution. As each dilution step completed, 0.05 ml of the resulting endotoxin dissolved physiological sline is added to every two of the heparin incorporated blood-collecting tube, so that the blood-collecting tubes were prepared which respectively contained endotoxin in concentrations of 8 EU/ml (Example 5), 80 EU/ml (Example 6), 800 EU/ml (Example 7), 8000 EU/ml (Example 8), 80000 EU/ml (Example 9) and 800000 EU/ml (Example 10) per a whole solution summing the heparin dissolved physiological saline and the endotoxin dissolved physiological saline.

Next, a butyl rubber-made stopper, which was configured to fit into the tube and had been previously washed well with an endotoxin-free water (manufactured by Otsuka Seiyaku Co.), was lightly placed at an opening of each blood-collecting tube so as not to tightly close the opening. Then, every blood-collecting tube was placed within a vacuum container. When an interior of the container was gradually reduced to a pressure of 570 mmHg, the opening of each blood-collecting tube was tightly closed by the stopper. The blood-collecting tubes thus prepared were employed as the containers for measurement of cell functions in Examples 5–10, respectively.

(2) Determination of Endotoxin Contents in The Blood-Collecting Tubes (Containers):

The endotoxin-free water (manufactured by Otsuka Seiyaku Co.) was introduced into an injector with a needle. The needle of injector was thrust into the butyl rubber-made stopper, as placed on each of the four vacuumed blood-collecting tubes which were obtained in the above (1) as containing heparin solely, to inject 0.9 ml of the endotoxin-free water (manufactured by Otsuka Seiyaku Co.) into each of the blood-collecting tubes, followed by agitation at 37° C. for 1 hour to extract endotoxin. Then, the endotoxin content in the extracted liquid was determined through a synthesized chromophoric substrate technique using a kit for the determination of endotoxin, ENDOSPECIE ES6 (product name) manufactured by Seikagaku Kogyo Co.

The results indicated the endotoxin content in the extracted liquid as being not greater than 0.05 EU/ml for each of the tested four blood-collecting tubes.

(3) Method for Determining TNFα and IL-1β Inducing Activities:

Using an injector with a needle, heparinized blood was collected from a usually healthy volunteer. The needle of injector was thrust into the butyl rubber-made stopper, as placed on each of the vacuumed blood-collecting tubes which were obtained in the above (1) as containing endotoxin in various concentrations, to inject 0.9 ml of the collected specimen blood into each of the blood-collecting tubes. Next, each of the blood-collecting tubes was mounted to a rocker platform for tumble mixing in a thermostatic chamber preheated to a temperature of 37° C. for subsequent tumble mixing for 4 hours. As the intimate mixing was completed, each blood-collecting tube was centrifuged at 1600 G at 4° C. for 10 minutes to collect a supernatant plasma. The collected plasma was determined for contents (pg/ml) of TNFα and IL-1β in the same manner as employed in Example 1.

Figure 4:
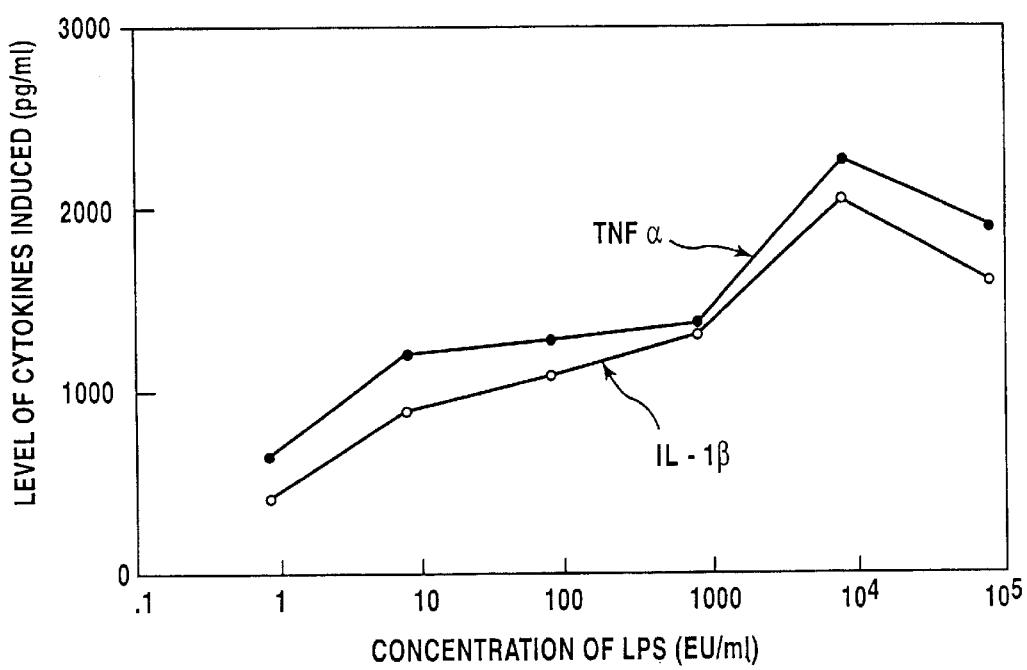
FIG. 4 is a graph showing measurement results obtained in Examples 5–10, wherein the abscissa indicates the concentration of LPS and the ordinate indicates the amount of TNFα or IL-1β induced.

The results are shown in FIG. 4. In FIG. 4, the unit EU/ml used for the LPS concentration on the abscissa indicates the endotoxin concentration in blood (in a whole solution) when in contact with blood, and the induced amount (pg/ml) on the ordinate indicates an average value of the values obtained from the two blood-collecting tubes for each of the TNFα and IL-1β concentrations in plasma. As apparent from the results, the endotoxin concentration in the range of 0.8–80000 EU/ml induces productions of TNFα and IL-1β. Also, when the endotoxin concentration is in the range of of 8–800 EU/ml, the amounts of TNFα and IL-1β induced are indicated as both increasing sluggishly. When the endotoxin concentration reaches 8000 EU/ml, the amounts of TNFα and IL-1β induced both indicated a further increase. However, when the endotoxin concentration reaches 80000 EU/ml, the amounts of TNFα and IL-1β induced each becomes smaller than when the endotoxin concentration is 8000 EU/ml.

The use of endotoxin, as illustrative of the cytokine-inducing material, in the range of 10–200 µg/ml (about 80000–2000000 EU/ml as converted to the endotoxin concentration) has been already described in the gazette of Patent Laying-open No. Hei 1-503331. However, the present invention enables use of endotoxin in lower concentrations, so that the cytokine induction via plural mechanisms does not occur which is believed due to higher concentrations of endotoxin. Therefore, in accordance with the present invention, it becomes possible to induce cytokines which accurately reflects the patients' morbidities.

Examples 11–16

(1) Method for Manufacturing A Container for Measurement of Cell Functions:

Each of 4 ml blood-collecting tubes (12.6×75 mm in diameter) made of polyethylene terephthalate was well washed 10 times with 4 ml of endotoxin-free water (manufactured by Otsuka Seiyaku Co.). 0.05 ml of a physiological saline for injection (manufactured by Otsuka Seiyaku Co.) containing heparin sodium (manufactured by Novo.Nordisk A/S Co., product name: Novo-Heparin # 1000) in a concentration of 200 U/ml was added to each tube.

E. coli 055:B5 derived endotoxin (manufactured by LBL corp.) was dissolved in a physiological saline for injection (manufactured by Otsuka Seiyaku Co.) to a concentration of 1600 EU/ml. 0.05 ml of the resulting endotoxin dissolved physiological sline solution was added to each of the above-prepared, heparin incorporated blood-collecting tubes.

Next, a butyl rubber-made stopper, which was configured to fit into the tube and had been previously washed well with an endotoxin-free water (manufactured by Otsuka Seiyaku Co.), was lightly placed at an opening of each blood-collecting tube so as not to tightly close the opening. Then, every blood-collecting tube was placed within a vacuum container. When an interior of the container was gradually reduced to a pressure of 570 mmHg, the opening of each blood-collecting tube was tightly closed by the stopper. The blood-collecting tubes thus prepared were employed as the containers for measurement of cell functions in Examples 11–16, respectively.

(2) Determination of Endotoxin Contents in The Blood-Collecting Tubes (Containers):

The endotoxin-free water (manufactured by Otsuka Seiyaku Co.) was introduced into an injector with a needle. The needle of injector was thrust into the butyl rubber-made stopper, as placed on each of the four vacuumed blood-collecting tubes which were obtained in the above (1) as containing heparin solely, to inject 0.9 ml of the endotoxin-free water (manufactured by Otsuka Seiyaku Co.) into each of the blood-collecting tubes, followed by agitation at 37° C. for 1 hour to extract endotoxin. Then, the endotoxin content in the extracted liquid was determined through a synthesized chromophoric substrate technique using a kit for the determination of endotoxin, ENDOSPECIE ES6 (product name) manufactured by Seikagaku Kogyo Co.

The results indicated the endotoxin content in the extracted liquid as being not greater than 0.05 EU/ml for each of the tested four blood-collecting tubes.

(3) Method for Determining TNFα and IL-1β Inducing Activities:

Using an injector with a needle, heparinized blood was collected from a usually healthy volunteer. The needle of injector was thrust into the butyl rubber-made stopper, as placed on each of the vacuumed blood-collecting tubes which were obtained in the above (1), to inject 0.9 ml of the collected specimen blood into each of the blood-collecting tubes. Next, two of the blood-collecting tube in which the specimen blood had been collected were mounted to each of the rocker platforms for tumble mixing respectively preheated to a temperature of 25° C. (Example 11), 30° C. (Example 12), 33° C. (Example 13), 37° C. (Example 14), 40° C. (Example 15), and 45° C. (Example 16) in a thermostatic chamber for subsequent tumble mixing for 4 hours. As the intimate mixing was completed, each blood-collecting tube was centrifuged at 1600 G at 4° C. for 10 minutes to collect a supernatant plasma. The collected plasma was determined for contents (pg/ml) of TNFα and IL-1β in the same manner as employed in Example 1.

Figure 5:
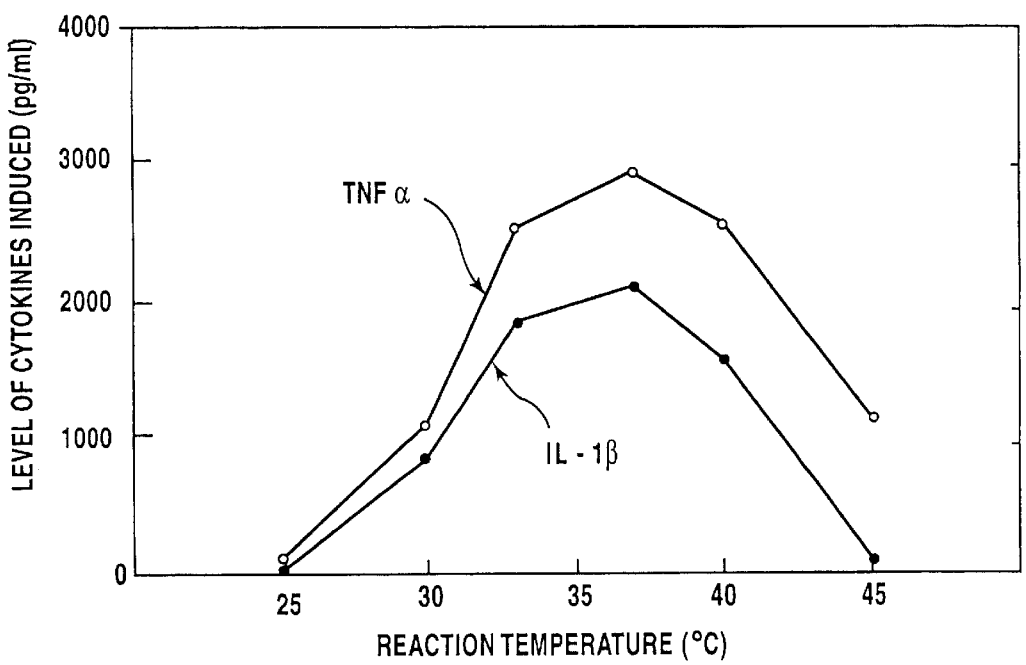
FIG. 5 is a graph showing measurement results obtained in Examples 11–16, wherein the abscissa indicates the reaction temperature and the ordinate indicates the amount of TNFα or IL-1β induced.

The results are shown in FIG. 5. In FIG. 5, the reaction temperature on the abscissa indicates the temperature at which the thermostatic chamber was set, and the induced amount (pg/ml) on the ordinate indicates an average value of the values obtained from the two blood-collecting tubes for each of the TNFα and IL-1β concentrations in plasma.

Examples 17–21

(1) Method for Manufacturing A Container for Measurement of Cell Functions:

Each of 4 ml blood-collecting tubes (12.6×75 mm in diameter) made of polyethylene terephthalate was well washed 10 times with 4 ml of endotoxin-free water (manufactured by Otsuka Seiyaku Co.). 0.05 ml of a physiological saline for injection (manufactured by Otsuka Seiyaku Co.) containing heparin sodium (manufactured by Novo.Nordisk A/S Co., product name: Novo-Heparin # 1000) in a concentration of 200 U/ml was added to each tube.

E. coli 055:B5 derived endotoxin (manufactured by LBL corp.) was dissolved in a physiological saline for injection (manufactured by Otsuka Seiyaku Co.) to a concentration of 1600 EU/ml. 0.05 ml of the resulting endotoxin dissolved physiological sline solution was added to each of the above-prepared, heparin incorporated blood-collecting tubes.

Next, a butyl rubber-made stopper, which was configured to fit into the tube and had been previously washed well with an endotoxin-free water (manufactured by Otsuka Seiyaku Co.), was lightly placed at an opening of each blood-collecting tube so as not to tightly close the opening. Then, every blood-collecting tube was placed within a vacuum container. When the interior of the container was gradually reduced to a pressure of 570 mmHg, the opening of each blood-collecting tube was tightly closed by the stopper. The blood-collecting tubes thus prepared were employed as the containers for measurement of cell functions in Examples 17–21, respectively.

(2) Determination of Endotoxin Contents in The Blood-Collecting Tubes (Containers):

The endotoxin-free water (manufactured by Otsuka Seiyaku Co.) was introduced into an injector with a needle. The needle of injector was thrust into the butyl rubber-made stopper, as placed on each of the four vacuumed blood-collecting tubes which were obtained in the above (1) as containing heparin solely, to inject 0.9 ml of the endotoxin-free water (manufactured by Otsuka Seiyaku Co.) into each of the blood-collecting tubes, followed by agitation at 37° C. for 1 hour to extract endotoxin. Then, the endotoxin content in the extracted liquid was determined through a synthesized chromophoric substrate technique using a kit for the determination of endotoxin, ENDOSPECIE ES6 (product name) manufactured by Seikagaku Kogyo Co.

The results indicated the endotoxin content in the extracted liquid as being not greater than 0.05 EU/ml for each of the tested four blood-collecting tubes.

(3) Method for Determining TNFα and IL-1β Inducing Activities:

Using an injector with a needle, haparinized blood was collected from a usually healthy volunteer. The needle of injector was thrust into the butyl rubber-made stopper, as placed on each of the 12 vacuumed blood-collecting tubes which were obtained in the above (1), to inject 0.9 ml of the collected specimen blood into each of the blood-collecting tubes. Next, the blood-collecting tubes in which the specimen blood had been collected were mounted to a rocker platform for tumble mixing preheated to a temperature of 37° C. in a thermostatic chamber for subsequent tumble mixing for 30 minutes (Example 17), 2 hours (Example 18), 4 hours (Example 19), 6 hours (Example 20), and 24 hours (Example 21), respectively. In the above Examples, two blood-collecting tubes for each Example were subjected to tumble mixing for the above-specified respective time period. As the intimate mixing was completed, each blood-collecting tube was centrifuged at 3000 rpm at 4° C. for 10 minutes to collect a supernatant plasma. The collected plasma was determined for contents (pg/ml) of TNFα and IL-1β in the same manner as in Example 1.

Figure 6:
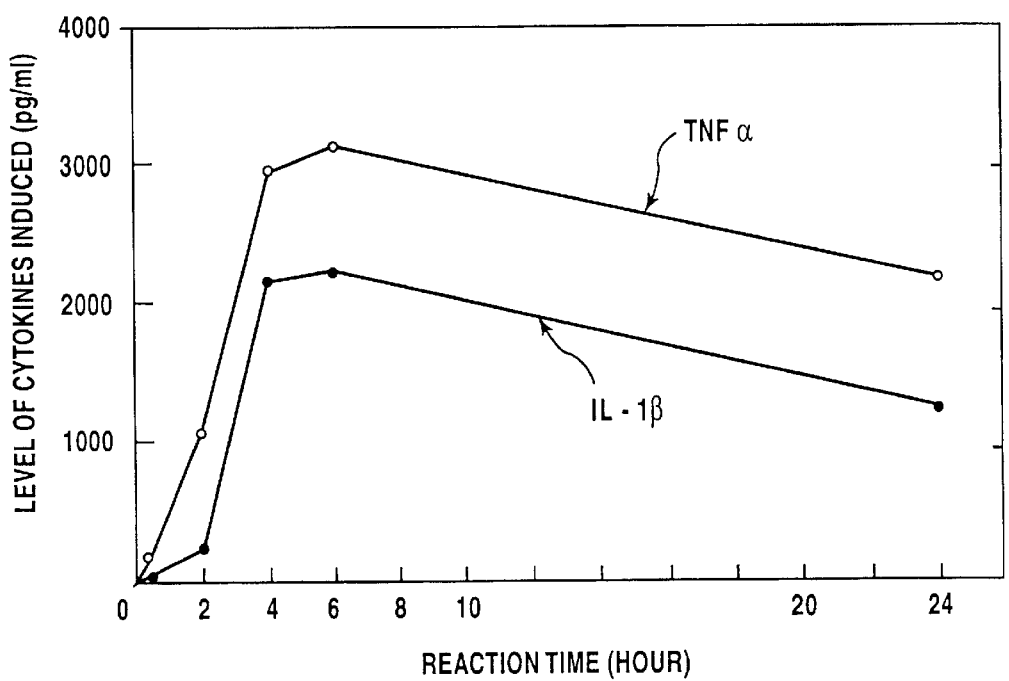
FIG. 6 is a graph showing measurement results obtained in Examples 17–21, wherein the abscissa indicates the reaction time and the ordinate indicates the amount of TNFα or IL-1β induced.

The results are shown in FIG. 6. In FIG. 6, the reaction time on the abscissa indicates the time period during which the above-described tumble mixing was performed, and the induced amount (pg/ml) on the ordinate indicates an average value of the values obtained from the two blood-collecting tubes for each of the TNFα and IL-1β concentrations in plasma.

EXAMPLE 22

(1) Method for Manufacturing A Container for Measurement of Cell Functions:

Each of 4 ml blood-collecting tubes (12.6×75 mm in diameter) made of polyethylene terephthalate was well washed 10 times with 4 ml of endotoxin-free water (manufactured by Otsuka Seiyaku Co.). 0.05 ml of a physiological saline for injection (manufactured by Otsuka Seiyaku Co.) containing heparin sodium (manufactured by Novo.Nordisk A/S Co., product name: Novo.Heparin # 1000) in a concentration of 200 U/ml was added to each tube.

Next, sterilized phytohemagglutinin-P (PHA-P) (manufactured by Sigma Chemical Co.) was dissolved in a physiological saline for injection (manufactured by Otsuka Seiyaku Co.). 0.05 ml of the resulting physiological sline solution was added to each of the above-prepared, heparin incorporated blood-collecting tubes, so that each blood-collecting tube contained PHA-P in concentrations of 100 μg/ml per a whole solution summing the heparin sodium dissolved physiological saline and the PHA-P dissolved physiological saline.

Then, a butyl rubber-made stopper, which was configured to fit into the tube and had been previously washed well with an endotoxin-free water (manufactured by Otsuka Seiyaku Co.) was lightly placed at an opening of each blood-collecting tube so as not to tightly close the opening. Then, every blood-collecting tube was placed within a vacuum container. When the interior of the container was gradually reduced to a pressure of 570 mmHg, the opening of each blood-collecting tube was tightly closed by the stopper. The vacuumed blood-collecting tubes thus prepared were respectively employed for the container for measurement of cell functions.

(2) Determination of Endotoxin Contents in The Blood-Collecting Tubes (Containers):

The endotoxin-free water (manufactured by Otsuka Seiyaku Co.) was introduced into an injector with a needle. The needle of injector was thrust into the butyl rubber-made stopper, as placed on each of the four vacuumed blood-collecting tubes which were obtain ed in the above (1) as containing heparin and PHA-P, to inject 0.9 ml of the endotoxin-free water (manufactured by Otsuka Seiyaku Co.) into each of the blood-collecting tubes, followed by agitation at 37° C. for 1 hour to extract endotoxin. Then, the endotoxin content in the extracted liquid was determined in the same manner as in Example 1. The results indicated the endotoxin content in the extracted liquid as being not greater than 0.05 EU/ml for each of the tested four blood-collecting tubes.

(3) Method for Determining TNFα, IL-1β and IL-6 Inducing Activities:

The TNFα, IL-1β and IL-6 inducing activities were determined in the same manner as in (3) of Example 1, except that the vacuumed blood-collecting tubes obtained in the above (1) as containing heparin and PHA-P were employed, instead of employing the vacuumed blood-collecting tubes which were obtained in (3) of Example 1 as containing endotoxin in various concentrations.

Comparative Example 5

(1) Method for Manufacturing A Container for Measurement of Cell Functions:

The vacuumed blood-collecting tubes containing heparin and PHA-P were manufactured in the same manner as in Example 22 (1) for employment as the containers for measurement of cell functions, except that the 4 ml vacuumed blood-collecting tubes (12.6×75 mm in diameter) made of polyethylene terephthalate, different from those employed in Example 22, were employed in place of the 4 ml vacuumed blood-collecting tubes (12.6×75 mm in diameter) made of polyethylene terephthalate as employed in Example 22.

(2) Determination of Endotoxin Contents in The Blood-Collecting Tubes (Containers):

The endotoxin content in each blood-collecting tube was determined in the same manner as in Example 22 (2), except that the four vacuumed blood-collecting tubes which were obtained in the above (1) as containing heparin and PHA-P were employed. The results indicated the endotoxin contents in the liquids respectively extracted in the tested four blood-collecting tubes as being 0.65 EU/ml, 0.74 EU/ml, 0.58 EU/ml and 0.62 EU/ml, respectively.

(3) Method for Determining TNFα, IL-1β and IL-6 Inducing Activities:

The TNFα, IL-1β and IL-6 inducing activities were determined in the same manner as in (3) of Example 22, except that 10 of the vacuumed blood-collecting tubes obtained in the above (1) as containing heparin and PHA-P were employed, instead of employing the vacuumed blood-collecting tubes prepared in (3) of Example 22 as containing heparin and PHA-P. The results are shown in Tables 1–3.

TABLE 1

|  |  |  | Exp. 22 | Comp. Exp. 5 |
|---|---|---|---|---|
| Level of TNFα Induced (pg/ml) | Blood-Collecting Tube No. | 1 | 452.8 | 684.5 |
| | | 2 | 420.5 | 790.5 |
| | | 3 | 468.5 | 948.6 |
| | | 4 | 440.2 | 664.5 |
| | | 5 | 495.6 | 895.3 |
| | | 6 | 462.8 | 980.5 |
| | | 7 | 442.1 | 728.6 |
| | | 8 | 432.8 | 894.2 |
| | | 9 | 489.2 | 925.1 |
| | | 10 | 438.8 | 696 |
| Mean Value (pg/ml) | | | 454.33 | 820.78 |
| SD* (pg/ml) | | | 24.5 | 120.9 |
| CV* (%) | | | 5.4 | 14.7 |

*SD = Standard Deviation
CV = Coefficient of Variation

TABLE 2

|  |  |  | Exp. 22 | Comp. Exp. 5 |
|---|---|---|---|---|
| Level of IL-1α Induced | Blood-Collecting Tube No. | 1 | 274.6 | 496.3 |
| | | 2 | 254.5 | 582.1 |
| | | 3 | 268.4 | 396.1 |

TABLE 2-continued

|  |  | Exp. 22 | Comp. Exp. 5 |
|---|---|---|---|
| (pg/ml) | 4 | 252.4 | 557.9 |
|  | 5 | 236.8 | 689.3 |
|  | 6 | 257.1 | 325.6 |
|  | 7 | 249.6 | 445.8 |
|  | 8 | 262.8 | 625.4 |
|  | 9 | 257.1 | 322.4 |
|  | 10 | 244.6 | 555.8 |
| Mean Value (pg/ml) |  | 255.79 | 499.72 |
| SD* (pg/ml) |  | 11.1 | 124.9 |
| CV* (%) |  | 4.3 | 25.0 |

*SD = Standard Deviation
CV = Coefficient of Variation

TABLE 3

|  |  |  | Exp. 22 | Comp. Exp. 5 |
|---|---|---|---|---|
| Level of IL-6 Induced (pg/ml) | Blood-Collecting Tube No. | 1 | 6820 | 8820 |
|  |  | 2 | 6930 | 12520 |
|  |  | 3 | 6240 | 9630 |
|  |  | 4 | 7150 | 13050 |
|  |  | 5 | 6420 | 9420 |
|  |  | 6 | 6390 | 8420 |
|  |  | 7 | 6980 | 7430 |
|  |  | 8 | 6520 | 12490 |
|  |  | 9 | 6480 | 10060 |
|  |  | 10 | 6610 | 9420 |
| Mean Value (pg/ml) |  |  | 6654 | 10126 |
| SD* (pg/ml) |  |  | 300 | 1910 |
| CV* (%) |  |  | 4.5 | 18.9 |

*SD = Standard Deviation
CV = Coefficient of Variation

As can be seen from Tables 1–3, the employment of containers for measurement of cell functions, which contain endotoxin in concentrations of not exceeding 0.5 EU/ml per extracted liquid, provided a better reproducibility.

Examples 23–30

(1) Method for Manufacturing A Container for Measurement of Cell Functions:

Each of 4 ml blood-collecting tubes (12.6×75 mm in diameter) made of polyethylene terephthalate was well washed 10 times with 4 ml of endotoxin-free water (manufactured by Otsuka Seiyaku Co.). Heparin sodium (manufactured by Novo.Nordisk A/S Co., product name: Novo.Heparin # 1000) and PHA-L (manufactured by Sigma Chemical Co.) were dissolved in a physiological saline (manufactured by Otsuka Seiyaku Co.) to prepare physiological saline solutions which contained 40 U/ml of heparin sodium and PHA-L in the concentrations shown in Table 4, respectively. 1 ml of respective physiological saline solutions was added to respective two of the blood-collecting tubes as washed above.

Next, a butyl rubber-made stopper, which was configured to fit into the tube and had been previously washed well with an endotoxin-free water (manufactured by Otsuka Seiyaku Co.), was lightly placed at an opening of each blood-collecting tube so as not to tightly close the opening. Then, every blood-collecting tube was placed within a vacuum container. When an interior of the container was gradually reduced to a pressure of 570 mmHg, the opening of each blood-collecting tube was tightly closed by the stopper. The blood-collecting tubes thus prepared were employed as the containers for measurement of cell functions in Examples 23–30, respectively.

(2) Determination of Endotoxin Contents in The Blood-Collecting Tubes (Containers):

1 ml of endotoxin-free water (manufactured by Otsuka Seiyaku Co.) was introduced into respective ones (8 in total) of the containers for measurement of cell functions which were obtained in the above (1) as containing various concentrations of PHA-L for subsequent agitation at 37° C. for 1 hour to extract endotoxin. Next, the endotoxin content in each extracted liquid was determined in the same manner as in Example 1. The results indicated the endotoxin content in the extracted liquid as being not greater than 0.05 EU/ml for each of the containers for measurement of cell functions.

(3) Method for Determining TNFα and IL-1β Inducing Activities:

Using an injector with a needle, heparinized blood was collected from a usually healthy volunteer. The needle of injector was thrust into the butyl rubber-made stopper, as placed on each of the containers for measurement of cell functions of Examples 23–30 respectively obtained in the above (1), to inject 1.0 ml of the collected specimen blood into each of the blood-collecting tubes. Next, each of the blood-collecting tubes was mounted to a rocker platform for tumble mixing in a thermostatic chamber preheated to a temperature of 37° C. for subsequent tumble mixing for 2 hours. As the intimate mixing was completed, each container was centrifuged at 1600 G at 4° C. for 10 minutes to collect a supernatant plasma. The collected plasma was determined for contents (pg/ml) of TNFα and IL-1β in the same manner as in (3) of Example 1. The results are shown in Table 4.

TABLE 4

|  |  | Inducer And Its Concentration (μg/ml) | | Cytokine Production (pg/ml) | |
|---|---|---|---|---|---|
|  |  | PHA-L | PHA-P | TNFα | IL-1β |
| Exp. | 23 | 0.02 | — |  | 5 |
|  | 24 | 0.2 | — | 70 | 80 |
|  | 25 | 2 | — | 2178 | 403 |
|  | 26 | 10 | — | 2864 | 563 |
|  | 27 | 50 | — | 2956 | 567 |
|  | 28 | 100 | — | 2431 | 432 |
|  | 29 | 200 | — | 2250 | 425 |
|  | 30 | 500 | — |  | 153 |
|  | 31 | — | 0.2 |  | 25 |
|  | 32 | — | 2 |  | 63 |
|  | 33 | — | 10 |  | 164 |
|  | 34 | — | 50 |  | 496 |

Examples 31–34

The procedure as practiced in Example 23 was repeated to quantitatively determine TNFα and IL-1β produced, except that PHA-P (manufactured by Sigma chemical Co.) was used in the concentrations shown in Table 4, instead of using PHA-L as in Example 23. The results are shown in Table 4. The endotoxin contents in the liquids, which were respectively extracted in containers for measurement of cell functions in Examples 31–34 in the same manner as done in (2) of Example 23, were not greater than 0.05 EU/ml.

Example 35 and Comparative Example 6

A commercially available vacuum blood-collecting tube, i.e. an LPS-free blood-collecting tube (manufactured by Sekisui chem. Ind. Co.: LPS free specification provided) was employed as the container for measurement of cell functions according to the first invention (Example 35). Also, another commercially available vacuum blood-collecting tube, i.e. a blood-collecting tube (LPS free specification unprovided) manufactured by A company was employed as the comparative blood-collecting tube (Comparative Example 6).

For each Example, blood was vacuum collected from an ordinarily healthy human (same person) into five blood-collecting tubes (1 ml each). Every blood-collecting tube was stored at 20° C. for 2 hours, and then centrifuged at 4° C. (1600 G, 10 minutes) for subsequent plasma collection. The amount of TNF-α in the collected plasma was determined using a product named "PREDICTA Human TNF-α ELISA KIT" manufactured by Genzyme Inc. The determined values were averaged to obtain a final value for each Example. The results indicated that the TNF-α concentration determined for Examples 35 was not greater than 15 pg/ml, i.e. a limit of detection, while that for Comparative Example 6 was 51 pg/ml.

The separate blood-collecting tubes from the same lot as the LPS-free blood-collecting tubes for use in Example 35 and those from the same lot as the blood-collecting tubes manufactured by A company for use in Comparative Example 6 were respectively determined for endotoxin contents in the manner which follows. 1 ml of an endotoxin-free water (manufactured by Otsuka Seiyaku Co.) was added to each of the above-specified blood-collecting tubes for subsequent agitation at 37° C. for 1 hour to extract endotoxin. Then, the endotoxin content in the extracted liquid in each tube was determined in the same manner as in Example 1. As a result, the endotoxin contents determined were 0.03 EU/ml in the collecting tube for use in Example 35 and 958 EU/ml in the collecting tube for use in Comparative Example 6.

As apparent from the above, in determining the TNFα concentration in blood, unless the blood is collected using the blood-collecting container in which the amount of endotoxin, when extracted by collecting endotoxin-free water of a volume equal to the liquid volume to be subjected to measurement, is rendered at a level insufficient to induce production of physiologically active substances from blood cells, the blood reacts with LPS in the blood-collecting container to produce (induce) the physiologically active substances such as TNFα, as well as being subjected to unnecessary stimulation to gradually change its properties, and as a result thereof the accurate determination of TNFα concentration in blood per se is hindered.

Example 36 and Comparative Examples 7–9

An LPS solution at a concentration of 120 ng/ml, as a stimulator, is distributed into 5 blood-collecting tubes for use in Example 35, 5 blood-collecting tubes for use in Comparative Example 6, 5 commercially available, heparin-incorporated vacuum blood-collecting tubes manufactured by B company and 5 commercially available, heparin-incorporated vacuum blood-collecting tubes manufactured by C company, i.e. 50 µl of the LPS solution for each blood-collecting tube, to prepare reactors for reacting LPS with blood to induce cytokines. The reactors prepared by using the blood-collecting tubes of Example 35 were assigned to Example 36, and those of Comparative Example 6 to Comparative Example 7, respectively. The reactors prepared by using the blood-collecting tubes manufactured by B company were assigned to Comparative Example 8, and those by C company to Comparative Example 9. In the meantime, the separate blood-collecting tubes from the same lot as the blood-collecting tubes manufactured by B company from which the reactors of Comparative Example 8 were prepared were separately determined for content of endotoxin in the same manner as in Example 35. Likewise, the separate blood-collecting tubes from the same lot as the blood-collecting tubes manufactured by C company from which the reactors of Comparative Example 9 were prepared were separately determined for endotoxin content in the same manner as in Example 35. The results indicated that the blood-collecting tubes manufactured respectively by B and C companies, for respective use in Comparative Examples 8 and 9, contained endotoxin in concentrations of 10 EU/ml and 389 EU/ml, respectively.

6 ml in total of heart blood was collected from 5 male, 8–10 weeks old ICR mice using an injector for subsequent injection into a blood-collecting container as identical to those used in Example 35.

The injector had been previously soaked in a 0.2 M aqueous solution of sodium hydroxide overnight in order to deactivate endotoxin, washed sufficiently with the endotoxin-free water, and further loaded with heparin in such an amount as to allow the blood after collected in the injector to finally contain heparin in a concentration of 10 U/ml.

Next, one needle portion of a multiple injector needle was thrust into a stopper of the above blood-collecting container and another needle portion thereof was thrust into one stopper after another stopper for the reactors for respective use in Example 36 and Comparative Examples 7–9 to distribute the collected blood into those reactors, i.e. 300 µl of collected blood for each reactor.

Each reactor was then maintained under agitation at 37° C. for 4 hours, and thereafter centrifuged (1600 G, 10 minutes) at 4° C. for subsequent collection of plasma. The amount of TNF-α in the collected plasma was determined using a product named "FACTOR TEST MOUSE TNF-β ELISA KIT" manufactured by Genzyme Inc. The determined values were averaged to obtain a final value for each Example. Also, the coefficient of variation (%) [=(standard deviation)/(average value)×100) was calculated for each Example. The results are given in Table 5.

TABLE 5

|  | TNFα Production | |
| --- | --- | --- |
|  | Mean Value (pg/ml) | CV* (%) |
| Exp. 36 | 1036 | 3.7 |
| Comp. Exp. 7 | 5610 | 23.7 |
| Comp. Exp. 8 | 1078 | 15.1 |
| Comp. Exp. 9 | 2961 | 10.5 |

*CV = Coefficient of Variation

As can be seen from Table 5, the least variance (coefficient of variation) in TNF-α production (induced) was observed in Example 36 wherein a known amount of LPS was added to the LPS-free blood-collecting container.

In view of the above results, in order to establish a measuring method whereby patients' morbidities and the others can be decided accurately and in a simplified manner, it is believed essential to store the collected blood without exposing it to unnecessary stimulation for a period from collection till subjected to measurements. To this end, it is necessary, when collecting blood, to employ a blood-collecting container which has a pressure-reduced interior and contains LPS in a level insufficient to permit physiologically active substances to be produced (released or induced), as can be clearly appreciated.

As also apparent from the above results, in order to accurately measure the functions of blood cells, it is necessary to employ a blood-collecting container which is not contaminated with endotoxin at a concentration sufficient to adversely affect measured values. It is also necessary to distribute the collected blood into blood-collecting containers each containing a predetermined amount of stimulator to thereby react blood collected with the stimulator for production (release or induction) of the physiologically active substances which are subsequently quantitatively determined.

Example 37

The instruments and containers for use in this Example were exposed to dry heating at 250° C. for 2 hours or longer, if made of glass, or alternatively, soaked in a 0.2 M aqueous solution of sodium hydroxide overnight to deactivate endotoxin and washed sufficiently with the endotoxin-free water, if made of plastics. Also, such an operation was performed within a clean bench.

10,000 Unit of heparin sodium (manufactured by Wako Junyaku Co.) was dissolved into 10 ml of physiological saline for injection (manufactured by Otsuka Seiyaku Co.). The resulting heparin sodium solution was subjected to centrifugal ultrafiltration at 500 G at 4° C. for 1 hour, using an ultrafilter CENTRIPREP 100 (fractional molecular weight 0.1 million, manufactured by Amicon Co.). The ultrafilter for use had been previously soaked in a 0.2 M aqueous solution of sodium hydroxide overnight to deactivate endotoxin and washed sufficiently with the endotoxin-free water.

The heparin sodium solution thus ultrafiltered was determined for endotoxin content, using ENDOSPECIE ES-6 (manufactured by Seikagaku Ind. Co.). The results indicated the endotoxin content in the heparin sodium solution as being 0.01 EU/heparin Unit.

Next, 0.1 ml of the ultrafiltered heparin sodium solution (1,000 U/ml) was added to a 10 ml blood-collecting injector (manufactured by Terumo Co.), supplemented with 10 ml of blood collected from an ordinarily healthy human volunteer (final heparin concentration in blood of about 10 U/ml). A blood fraction immediately after collection, as well as another blood fraction left to stand in a thermostatic chamber at 37° C. for 2 hours and 4 hours, were respectively centrifuged at 1600 G at 4° C. for 10 minutes to collect a supernatant plasma for each.

The collected plasma was determined for contents of cytokines, i.e. TNFα, IL-1β and IL-6 contents, using enzyme immunoassay kits containing respective monoclonal antibodies against those cytokines. The determination of each cytokine content was carried out using n=3, and the obtained average value thereof is shown in Table 6.

Comparative Example 10

The blood collection was carried out in the same manner as in Example 37, except that the heparin sodium solution employed was not subjected to an ultrafiltration treatment. The collected plasma was determined for contents of cytokines, i.e. TNFα, IL-1β and IL-6 contents, using enzyme immunoassay kits containing respective monoclonal antibodies against those cytokines. The determination of each cytokine content was carried out using n=3, and the obtained average value thereof is shown in Table 6.

Besides, the heparin sodium solution as employed in this Comparative Example 10 was determined for endotoxin content in the same manner as in Example 37. The results indicated it as being 1.2 EU/heparin Unit.

TABLE 6

|  |  | *Immediately (pg/ml) | *2 Hrs. (pg/ml) | *4 Hrs. (pg/ml) |
|---|---|---|---|---|
| Exp. 37 | TNFα | 35 | 35 | 35 |
|  | IL-1α | 15 | 15 | 15 |
|  | IL-6 | 35 | 35 | 35 |
| Comp. Exp. 10 | TNFα | 35 | 2850 ± 298 | 6580 ± 596 |
|  | IL-1β | 15 | 548 ± 42 | 3490 ± 412 |
|  | IL-6 | 35 | 1225 ± 179 | 4865 ± 329 |

*Time period After Blood Collection

As apparent from Table 6, in the system using the ultrafiltered heparin sodium solution wherein the endotoxin content was reduced to 0.01 EU/heparin Unit (endotoxin concentration in blood of about 0.1 EU/ml), neither of TNFα, IL-1β and IL-6 was produced in an appreciable amount until 4 hours elapsed from the blood collection. On the other hand, in the system using the untreated heparin sodium solution wherein the endotoxin content was 1.2 EU/heparin Unit (endotoxin concentration in blood of about 12 Eu/ml), due to the presence of an appreciable amount of endotoxin, the increased amounts of TNFα, IL-1β and IL-6 were produced in blood with time.

Examples 38–40

The instruments and containers for use in this Example were exposed to dry heating at 250° C. for 2 hours or longer, if made of glass, or alternatively, soaked in a 0.2 M aqueous solution of sodium hydroxide overnight to deactivate endotoxin and washed sufficiently with the endotoxin-free water, if made of plastics. Also, the operation was carried out within a clean bench.

A 0.01 ml solution containing 10 Units of heparin sodium prepared in Example 37 as containing endotoxin in a concentration of 0.01 EU/heparin Unit was added to each of endotoxin-free, 5 ml blood-collecting tubes (12.6×75 mm in diameter, manufactured by Sekisui Chem. Ind. Co.) made of polyethylene terephthalate.

Next, *E. coli* UKT-B derived, standard endotoxin of Japanese pharmacopeia was dissolved in 1.6 ml of a physiological saline for injection for subsequent stepwise dilution. As each dilution step completed, the resulting endotoxin dissolved physiological sline is added to the heparin sodium incorporated blood-collecting tubes, so that the blood-collecting tubes were prepared which respectively contained endotoxin in concentrations of 0.1 EU/ml (Example 38), 0.2 EU/ml (Example 39) and 0.4 EU/ml (Example 40) per collected blood.

Then, a butyl rubber-made stopper, which was configured to fit into the blood-collecting tube, was lightly placed at an opening of each blood-collecting tube so as not to tightly close the opening. Then, every blood-collecting tube was placed within a pressure-reducible container. When the interior of the container was reduced to a pressure sufficient to suction 1 ml of blood, the opening of each blood-collecting tube was tightly closed by the stopper.

Next, blood was vacuum collected from a usually healthy volunteer into the blood-collecting tubes, i.e. 1 ml per each. Each of the blood-collecting tubes was mounted to a rocker platform for tumble mixing in a thermostatic chamber preheated to a temperature of 37° C. for subsequent tumble mixing for 2 hours. As the intimate mixing was completed, each tube was centrifuged at 1600 G at 4° C. for 10 minutes to collect a supernatant plasma.

The collected plasma was determined for contents of cytokines, i.e. respective contents of TNFα, IL-1β and IL-6 in the same manner as in Example 37. The determination of each cytokine content was carried out using n=3, and the obtained average value thereof is shown in Table 7.

Comparative Examples 11, 12

The procedure of Example of 38 was repeated to collect blood, except that the prepared endotoxin dissolved physiological saline solution was added to the heparin sodium incorporated blood-collecting tubes, so that the blood-collecting tubes were prepared which respectively contained endotoxin in concentrations of 0.5 EU/ml (Comparative Example 11) and 1.0 EU/ml (Comparative Example 39) per blood-collecting tube.

The collected plasma was determined for contents of cytokines, i.e. respective contents of TNFα, IL-1β and IL-6 in the same manner as in Example 37. The determination of each cytokine content was carried out using n=3, and the obtained average value thereof is shown in Table 7.

TABLE 7

|  | *Endotoxin (EU/ml) | TNFα (pg/ml) | IL-1β (pg/ml) | IL-6 (pg/ml) |
| --- | --- | --- | --- | --- |
| Exp. | 38 0.1 | 35 | 15 | 35 |
|  | 39 0.2 | 35 | 15. | 35 |
|  | 40 0.4 | 35 | 15 | 35 |
| Comp. | 11 0.5 | 485 ± 29 | 154 ± 12 | 189 ± 21 |
| Exp. | 12 1.0 | 3560 ± 398 | 1548 ± 162 | 2225 ± 279 |

*Concentration in Blood

As apparent from Table 7, if the endotoxin content in blood exceeds 0.5 EU/ml, it induces productions of TNFα, IL-1β and IL-6.

Example 41

<Method for Manufacturing A Kit for Measurement of Cell Functions>

Heparin sodium (manufactured by Novo-Nordisk A/S Co., product name: NOVO.HEPARIN #1000) was diluted with an endotoxin-free water (manufactured by Otsuka Seiyaku Co.) to obtain a heparin sodium solution containing heparin in a concentration of 200 U/ml. 0.05 ml of the heparin sodium solution was added to the blood-collecting tube, which had been prepared in Example 1 as containing endotoxin in a concentration of not greater than 0.05 EU, so that the blood-collecting tube contained 10 Units of heparin. The resulting solution was vacuum dried. Then, a butyl rubber-made stopper, which was configured to fit into the blood-collecting tube, was lightly placed at an opening of the blood-collecting tube so as not to tightly close the opening. The blood-collecting tube was then placed within a pressure-reducible container. When the interior of the container was reduced to a pressure sufficient to suction 1 ml of blood, i.e. to a pressure of 570 mmHg, the opening of blood-collecting tube was tightly closed by the stopper. The first container for measurement of cell functions was thus manufactured.

Heparin sodium (manufactured by Novo.Nordisk A/S Co., product name: NOVO.HEPARIN #1000) was diluted with an endotoxin-free water (manufactured by Otsuka Seiyaku Co.) to obtain a heparin sodium solution containing heparin in a concentration of 200 U/ml. Meanwhile, E. Coli. 055:B5 derived endotoxin (manufactured by LBL Co.) was diluted with an endotoxin-free water to obtain an endotoxin dissolved solution containing endotoxin in a concentration of 2,000 EU/ml. 0.05 ml of the heparin sodium solution was added to the blood-collecting tube, which had been prepared in Example 1 as containing endotoxin in a concentration of not greater than 0.05 EU, so that the blood-collecting tube contained 10 Units of heparin. 0.05 ml of the endotoxin dissolved solution was subsequently added to the blood-collecting tube. The resulting solution was vacuum dried. Then, a butyl rubber-made stopper was lightly placed at an opening of the blood-collecting tube so as not to tightly close the opening. The blood-collecting tube was then placed within a pressure-reducible container. When the interior of the container was reduced to a pressure sufficient to suction 1 ml of blood, i.e. to a pressure of 570 mmHg, the opening of blood-collecting tube was tightly closed by the stopper. The second container for measurement of cell functions was thus manufactured.

The first and second reagents for TNFα determination were manufactured in accordance with the procedures which follow.

Anti-human TNFα monoclonal antibody (manufactured by Genzyme Inc.) was diluted with a 0.1 M carbonate buffer (pH 9.5) to obtain a dilute solution in a concentration of 1 μg/ml (immobilized antibody solution for the first TNFα determination reagent, i.e. for high sensitivity determination) and a dilute solution in a concentration of 100 ng/ml (immobilized antibody solution for the second TNFα determination reagent, i.e. for low sensitivity determination), respectively. 100 μl of each dilute solution was added to each well of an 96 well microplate (Nunc MaxiSorp microtiter plates) for subsequent incubation at 2–8° C. for one day and one night. Next, each well was suction washed 3 times with a phosphate buffer (pH 7.3) containing 0.05 weight % of Tween 20. Then, 250 μl of a phosphate buffer (pH 7.3) containing 4 weight % of bovine serum albumin (manufactured by Sigma Chemical Co.) was added to each well for subsequent incubation at 37° C. for 2 hours. The incubated solutions were then removed from every well of the microplate which was subsequently dried at room temperature.

Besides, commercially available reagents were used for human TNFα (manufactured by Genzyme Inc.), viotin-labelled anti-human TNFα polyclonal antibody (manufactured by Genzyme Inc.), hydrogen peroxide, and a substrate solution containing tetramethylbenzidine (manufactured by KPL Co.). Also, a phosphate buffer (pH 7.3) containing 0.05 weight % of Tween 20 was used as a washing solution. A 2 M solution of sulfuric acid was prepared to use as a stop solution.

<Measurement of TNFα-Producing Capacities>

An injector with a needle was employed to collect heparinized blood from an ordinarily healthy volunteer. The needle was successively thrust into butyl rubber-made stoppers for the respective first and second containers for measurement of cell functions to inject 1 ml of specimen blood into each container. Next, each of the containers accommodating blood was mounted to a rocker platform for tumble mixing placed in a thermostatic chamber preheated to a temperature of 37° C. for subsequent tumble mixing for 4 hours. As the intimate mixing was completed, each tube was centrifuged at 1,600 G at 4° C. for 10 minutes to collect a supernatant plasma. The plasma collected from the first container for measurement of cell functions was distributed into 4 wells for determination of TNFα content in the same manner as in (3) of Example 1, using the above-specified high sensitivity reagent. On the other hand, the plasma collected from the second container for measurement of cell functions was distributed into 4 wells for determination of TNFα content in the same manner as in (3) of Example 1, using the above-specified low sensitivity reagent.

Comparative Example 13

The production of TNFα was induced in the same manner as in Example 41 in each of the first and second containers for measurement of cell functions, and plasma collected from each of them was distributed into 4 wells for determination of TNFα content in plasma using a commercially available kit (PREDICTA Human TNF-α KIT). When the measured values exceeded its limit of detection, the collected plasma was diluted with a phosphate buffer (pH 7.3) containing 1 weight % of bovine serum albumin at a dilution ratio of about 5 for another measurement. The TNFα contents were measured by multiplying the measured values by the dilution ratio.

The results from Example 41 and Comparative Example 13 are given in the following Table 8.

TABLE 8

| | [TNFα Concentration in Plasma (pg/ml) : Mean Value ± SD, CV (%)] | | | |
|---|---|---|---|---|
| | No. 1 | No. 2 | No. 3 | No. 4 |
| Exp. 41 | | | | |
| 2nd Container for Measurement of Cell Functions | 3870 ± 280, 7.2 | 2570 ± 180, 7.0 | 4870 ± 380, 7.8 | 4520 ± 340, 7.5 |
| 1st Container for Measurement of Cell Functions | <*LD | <*LD | <*LD | <*LD |
| Comp. Exp. 13 | | | | |
| 2nd Container for Measurement of Cell Functions | 2520 ± 400, 15.8 | 2070 ± 310, 14.9 | 4510 ± 620, 13.7 | 4020 ± 780, 19.4 |
| 1st Container for Measurement of Cell Functions | <*LD | <*LD | <*LD | <*LD |

*LD = Limit of Detection

In Table 8, CV denotes a coefficient of variation.

As clear from the results in Table 8, the commercial kit can not be used in determining the amount of TNFα0 induced in the second container for measurement of cell functions before the dilution operation is practiced. The Example gave the results higher in reproducibility, i.e. the coefficients of variation of around 7.5%. On the other hand, the Comparative Example, in which the measurement of TNFα contents were carried out by the commercial kit after plasma dilution, gave the results lower in reproducibility, i.e., the coefficients of variation ranged from about 15 to about 20%.

EFFECTS OF THE INVENTION

In accordance with the first invention of the present application, in the container for measurement of cell functions, for use in determining physiologically active substances produced from blood cells, the container is characterized in that the amount of material capable of inducing production of the physiologically active substances, when extracted by collecting water of a volume equal to a liquid volume to be subjected to measurement, is limited to a level insufficient to induce production of the physiologically active substances from the blood cells. Accordingly, the collected blood is scarcely subjected to unnecessary stimulation for a period from collection till measurement so that a long-term preservation thereof is enabled. This allows precise measurement of the physiologically active substances present in the collected blood and enables the use of the container in precisely examining morbidities of patients having various diseases.

Also, the container for measurement of cell functions in accordance with the first invention can be suitably employed to obtain control values, when used in combination with the container for measurement of cell functions in accordance with the second invention.

In the container for measurement of cell functions in accordance with the first invention of the present application, in the case where the material capable of inducing production of the above-described physiologically active substances is endotoxin, the endotoxin content in the container for measurement of cell functions before use is preferably controlled not to exceed 0.5 EU/ml as a concentration in an extracted liquid when extracted by collecting water of a volume equal to a liquid volume to be subjected to measurement. This allows precise measurement of the physiologically active substances present in the collected blood without being disturbed by the endotoxin content in the container before blood collection.

In the container for measurement of cell functions in accordance with the second invention, although the material capable of inducing production of the physiologically active substances in blood is accommodated in such a condition as being contactable with blood, the content of the material capable of inducing production of the physiologically active substances, originally present in the container before accommodation thereof, is limited to a level insufficient to influence measured values of the physiologically active substances. Accordingly, the production of physiologically active substances can be determined very accurately when the blood is introduced and contacted with the material capable of inducing production of the physiologically active substances to thereby produce the physiologically active substances.

Also, in the container for measurement of cell functions in accordance with the second invention, if the material which induces production of the above-described physiologically active substances is endotoxin, the endotoxin concentration in a resulting whole liquid when contacted with blood is limited as being in the range of 0.6–100,000 EU/ml. Accordingly, the production of physiologically active substances can be determined very accurately when the blood is introduced and contacted with the material capable of inducing production of the physiologically active substances to thereby produce the physiologically active substances.

In the container for measurement of cell functions in accordance with the first or second invention, the further accommodation of anticoagulants serves to prevent blood coagulation in the container for measurement of cell functions.

Also, when the amount of the material capable of inducing production of physiologically active substances contained in the above-described anticoagulant is controlled at a level insufficient to induce production of the physiologically active substances from blood cells when mixed with blood, the physiologically active substances produced can be determined very accurately without being influenced by the physiologically active substance-inducing materials originally contained in the anticoagulant.

Also, in the container for measurement of cell functions in accordance with the first or second invention, the reduction in pressure of the interior of container facilitates introduction of blood into the container for measurement of cell functions. Accordingly, the operations are not required which include manually transferring the blood to various reactors as by pipetting subsequent to blood collection from an examined human, cell separation, cell culture and the others. This eliminates a risk for an examining person to acquire various infectious diseases, such as hepatitis and AIDS. Also, the endotoxin content in the container before use is limited to thereby eliminate a possibility that various bacteria or dusts are accidentally incorporated into a specimen blood. The potential problem of causing unnecessary activation or activation drop of cells due to the presence of contaminants or the practice of various operations is thus avoided. Also, since a whole blood is used, the specialized techniques are not required which include separation and culture of cells, microscopic measurement and the others. This shortens the time period for measurement and eliminates the necessity of introducing RI facilities and expensive equipments such as a flow cytometer. As a result, the measurement of cell functions can be carried out which is more simplified in operation, less costly and more accurate than conventional.

In the kit for measurement of cell functions according to the present invention which includes the containers for measurement of cell functions according to the first and second inventions and the reagent capable of quantitatively determining the induced physiologically active substances, the use of the above-defined quantitatable reagent enables ready quantification of the induced physiologically active substances.

Also, the third invention of the present application includes the container for measurement of cell functions according to the first invention, the container for measurement of cell functions according to the second invention, and the reagent for quantitatively determining the physiologically active substances. Accordingly, when the blood is introduced into both the first and second containers for measurement of cell functions for the quantitatation by the above-specified reagent, the control value can be obtained from the first container for measurement of cell functions while the measured values corresponding to the amount of physiologically active substances induced in blood by the physiologically active substance-inducing material. As a result, the highly precise quantification of the physiologically active substances in blood is enabled.

In such a case, the first and second enzyme immunoassay reagents having different sensitivities from each other can be used for the first and second containers for measurement of cell functions, respectively, according to the intended purposes thereof. This enables precise quantification of the induced physiologically active substances.

Also, in the kit for measurement of cell functions in accordance with the third invention, if the physiologically active substance-inducing material is endotoxin, the endotoxin content in the second container is controlled such that the concentration of endotoxin in a resulting whole liquid when contacted with blood is in the range of 0.6–100,000 EU/ml. As a result, the amount of physiologically active substances produced in blood when endotoxin was contacted with the blood can be determined very accurately.

In the method for measurement of cell functions in accordance with the fourth invention of the present application, blood is introduced into the container for measurement of cell functions, according to the second invention, and contacted with the physiologically active substance-inducing material in order to induce the physiologically active substances. Since the endotoxin content in the container for measurement of cell functions according to the second invention is limited to the above-specified range, the amount of physiologically active substances produced in blood can be determined very accurately.

In this case, the production of the physiologically active substances can be reliably induced by inducing production of physiologically active substances at a temperature in the 26–45° C. range, or alternatively, by inducing production of physiologically active substances over the time period of 1–6 hours.

In the method for measurement of cell functions in accordance with the fourth invention, the amount of the physiologically active substances produced in blood can be reliably determined by quantitating the physiologically active substances using the reagent capable of quantitatively determining them.

What is claimed is:

1. A kit for measurement of cell functions comprising:
   a first container for measurement of cell functions by determining a physiologically active substance produced by blood cells, said container comprising at least a wall made of a first container material defining a space inside the first container and an amount of a first inducer contained in the container material, wherein the first inducer is capable of inducing production of said physiologically active substance, wherein said amount is such that, when a volume of an aqueous liquid for said measurement of cell functions is introduced into said first container, a resulting concentration of said inducer in said aqueous liquid is insufficient to induce the production of the physiologically active substance by the blood cells;
   a second container for measurement of cell functions, said second container having an identical structure to the first container and comprising at least a wall made of a second container material defining a space inside the second container, a first amount of the first inducer contained in the second container material, and a second amount of the first inducer and/or a second inducer in said space inside the second container, wherein said inducer is capable of inducing production of a physiologically active substance in blood when said inducer is in contact with the blood, wherein said first amount is such that, when a volume of an aqueous liquid for said measurement of cell functions is introduced into said second container in the absence of said second amount, a resulting concentration of said inducer in said aqueous liquid is insufficient to induce the production of the physiologically active substance by the blood cells, and also wherein said second amount is such that, when the blood is introduced into the container, a resulting concentration of said inducer is sufficient to induce the production of the physiologically active substance in the blood; and
   a reagent for quantitating said physiologically active substance;

each of said first and second containers, having an opening and further comprising a stopper to seal the opening, wherein the stopper is not removed when the blood is collected.

2. The kit for measurement of cell functions as recited in claim 1, further comprising an anticoagulant contained therein.

3. The kit for measurement of cell functions as recited in claim 1, wherein the space inside the first or second container is reduced in pressure to a level lower than an atmospheric pressure.

4. The kit for measurement of cell functions as recited in claim 1, wherein said physiologically-active substance is a cytokine.

5. The kit for measurement of cell functions as recited in claim 1, wherein said physiologically-active substance is at least one member selected from the group consisting of tumor necrosis factor α, interleukin-1β, and interleukin-6.

6. The kit for measurement of cell functions as recited in claim 1, the space inside the first container and the space inside the second container are reduced in pressure to a level below an atmospheric pressure.

7. The kit for measurement of cell functions as recited in claim 1, wherein at least one of said first and second container further comprising an anticoagulant contained therein.

8. The kit for measurement of cell functions as recited in claim 1, wherein said regent includes:
 a first regent used in a first enzyme immunoassay for quantitatively determining the physiologically active substance in the aqueous liquid introduced in the first container for measurement of cell functions, wherein said enzyme functions as a label in the enzyme immunoassay, wherein said aqueous liquid is blood;
 a second regent used in a second enzyme immunoassay for quantitatively determining the physiologically active substance produced by the inducer in the second container for measurement of cell functions, wherein said enzyme functions as a label in the enzyme immunoassay, the second enzyme immunoassay having a different sensitivity for the quantitative determination of the physiologically active substance than the first enzyme immunoassay.

9. The kit for measurement of cell functions as recited in claim 1, wherein said first inducer is endotoxin and said amount of endotoxin contained the respective container material does not exceed 0.5 EU/ml.

10. The kit for measurement of cell functions recited in claim 1, wherein said first and second inducer capable of inducing production of the physiologically active substance is endotoxin, and wherein said resulting concentration of inducer in said mixture in the second container for said measurement of cell functions is in the range of 0.6–100,000 EU/ml.

11. The kit for measurement of cell functions as recited in any one of claims 1–8, said physiologically-active substance is a cytokine.

12. The kit for measurement of cell functions as recited in any one of claims 1–8, said physiologically-active substance is at least one member selected from the group consisting of tumor necrosis factor α, interleukin-1β, and interleukin-6.

* * * * *